US012646588B2

(12) United States Patent
Chen et al.

(10) Patent No.: US 12,646,588 B2
(45) Date of Patent: Jun. 2, 2026

(54) DNA MOVABLE TYPE STORAGE SYSTEM AND METHOD

(71) Applicant: BEIJING INSTITUTE OF GENOMICS CHINESE ACADEMY OF SCIENCES / CHINA NATIONAL CENTER FOR BIOINFORMATION, Beijing (CN)

(72) Inventors: Fei Chen, Beijing (CN); Dongbo Bu, Beijing (CN); Guannan Ma, Beijing (CN); Chenyang Wang, Beijing (CN); Jing Xing, Beijing (CN)

(73) Assignee: BEIJING INSTITUTE OF GENOMICS CHINESE ACADEMY OF SCIENCES / CHINA NATIONAL CENTER FOR BIOINFORMATION, Beijing (CN)

( * ) Notice: Subject to any disclaimer, the term of this patent is extended or adjusted under 35 U.S.C. 154(b) by 671 days.

(21) Appl. No.: 18/016,272

(22) PCT Filed: Jun. 7, 2021

(86) PCT No.: PCT/CN2021/098663
§ 371 (c)(1),
(2) Date: Jan. 13, 2023

(87) PCT Pub. No.: WO2022/012216
PCT Pub. Date: Jan. 20, 2022

(65) Prior Publication Data
US 2023/0274793 A1 Aug. 31, 2023

(30) Foreign Application Priority Data
Jul. 16, 2020 (CN) ......................... 202010688281.X

(51) Int. Cl.
*G16B 30/20* (2019.01)
*G06N 3/123* (2023.01)

(52) U.S. Cl.
CPC ............. *G16B 30/20* (2019.02); *G06N 3/123* (2013.01)

(58) Field of Classification Search
None
See application file for complete search history.

(56) References Cited

U.S. PATENT DOCUMENTS

| | | | | |
|---|---|---|---|---|
| 10,423,341 B1 * | 9/2019 | Kermani | ............... | G06F 3/0631 |
| 2007/0117094 A1 * | 5/2007 | Hayashizaki | .......... | C12N 11/12 435/6.14 |

(Continued)

FOREIGN PATENT DOCUMENTS

| | | | | | |
|---|---|---|---|---|---|
| CN | 104850760 | A | * | 8/2015 | |
| CN | 110427786 | A | * | 11/2019 | ........... G06F 21/602 |

(Continued)

OTHER PUBLICATIONS

International Search Report issued in corresponding International Application No. PCT/CN2021/098663, mailed Aug. 26, 2021; 7 pgs.

(Continued)

*Primary Examiner* — Haimei Jiang
(74) *Attorney, Agent, or Firm* — HAUPTMAN HAM, LLP

(57) ABSTRACT
A DNA movable type storage system and method based on movable type printing including: (1) construct a physical DNA movable type library of data payloads and a physical DNA movable type library of indexes based on "DNA movable type codebook", which consist of a variety of DNA oligonucleotides corresponding to all "DNA payload movable type elements" and "DNA index movable type ele- (Continued)

MT: Movable Type ments" in the two libraries, respectively; (2) transcode from the storage binary data into corresponding "DNA movable type units", each of which contains corresponding DNA payload movable type elements and related DNA index movable type elements; (3) link the abovementioned DNA payload and index movable type elements to form a physical "DNA movable type unit", and put all generated DNA movable type units together for DNA storage, which cover all data information of the target file.

9 Claims, 4 Drawing Sheets

Specification includes a Sequence Listing.

(56) References Cited

U.S. PATENT DOCUMENTS

2018/0225177 A1 * 8/2018 Bhagi ................... G06F 16/164
2020/0063127 A1 * 2/2020 Lu ............................. C12N 9/78

FOREIGN PATENT DOCUMENTS

CN        111091876 A * 5/2020  .............. G16B 30/00
CN        111858510 A * 10/2020  ........... G06F 16/172

OTHER PUBLICATIONS

Written Opinion issued in corresponding International Application No. PCT/CN2021/098663, mailed Aug. 26, 2021; 7 pgs.

* cited by examiner

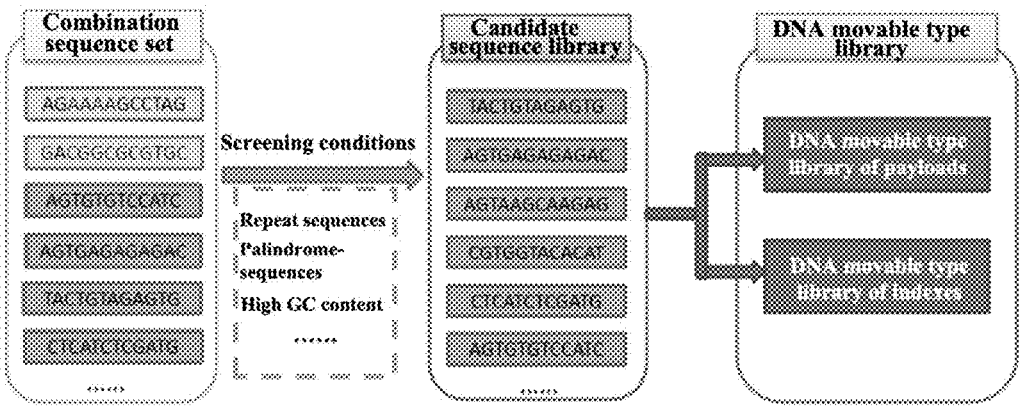
Fig. 4
Correspondance
| | | |
|---|---|---|
| 1. | 0000 0000 | ATACCCGGA |
| 2. | 0000 0001 | ACTGATGCG |
| 3. | 0000 0010 | GCATGCTAC |
| 4. | 0000 0011 | CTAGCCGTT |
| | ...... | ...... |
| 253. | 1111 1100 | ACTGTTCGA |
| 254. | 1111 1101 | TCGGGAACG |
| 255. | 1111 1110 | TTTAATCGG |
| 256. | 1111 1111 | GTAGCTGAAG |
Fig. 5
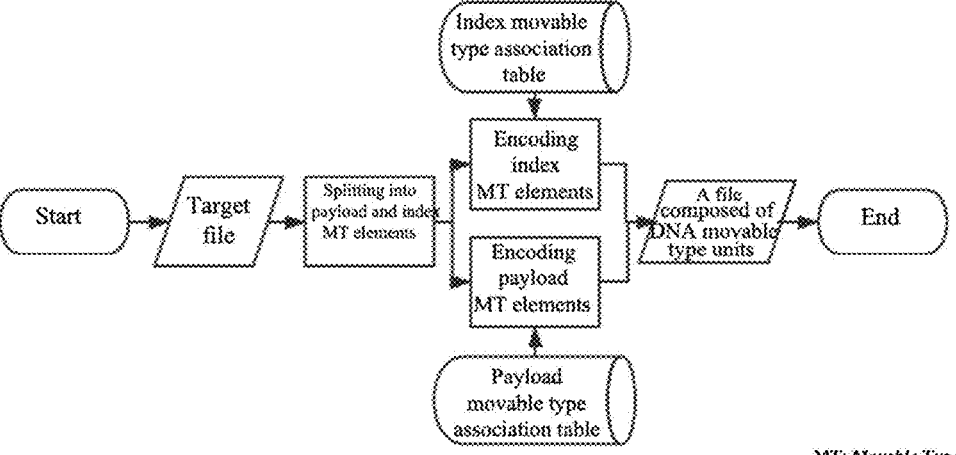
MT: Movable Type
Fig. 6

DNA MOVABLE TYPE STORAGE SYSTEM AND METHOD

RELATED APPLICATIONS

The present application is a U.S. National Phase of International Application Number PCT/CN2021/098663 filed Jun. 7, 2021 and claims priority to Chinese Application Number 202010688281.X filed Jul. 16, 2020.

INCORPORATION BY REFERENCE

The sequence listing provided in the file entitled Sequence_listing_PCTCN2021098663.txt, which is an ASCII text file that was created on Jan. 13, 2023, and which comprises 46,887 bytes, is hereby incorporated by reference in its entirety.

TECHNICAL FIELD

The disclosure relates to the field of DNA storage, in particular to a storage system and method based on the concept of DNA movable type.

BACKGROUND ART

As an emerging big data storage technology, DNA storage technology breaks through the limitation of the existing storage medium of silica-based materials, such as hard disks, optical disks and removable disks. Taking advantage of the inherent information storage capacity of DNA, DNA storage technology, according to certain encoding methods/rules, converts the 0-1 binary codes encoding various data files (text, image, audio, video, etc.) to corresponding DNA quaternary codes (i.e., combinations of A, T, C, and G), and the corresponding DNAs are then synthesized to store the data information into the DNA oligonucleotides with specific sequences. Conversely, based on corresponding decoding methods/rules, the stored DNAs can be sequenced to obtain DNA quaternary codes, further restoring to the data files with 0-1 binary codes. In short, DNA storage technology can achieve the data encoding, storage and reading using the synthesized DNAs with specific sequences based on certain encoding and decoding methods (i.e., codebook). Compared with the existing data and information storage technologies, DNA storage technology has the advantages of high data density, long storage time, low energy consumption, convenience for carrying, concealed transportation, and multiple encryptions The idea of storing data and information using DNA was proposed early, however, the DNA storage technology did not have a substantial progress until 2005, with the rapid development of high-throughput DNA synthesis technologies and sequencing technologies. In 2007, Nozomu Yachie et al. for the first time, succeeded to realize the DNA storage for the text data of Einstein's "E=mc^2 1905!" using a hexadecimal transcoding technology, incorporated herein by reference. In August 2012, George Church's research group published a milestone research on DNA storage in the journal *Science*, for the first time, they used a DNA chip as data storage medium, and successfully stored a variety of media files (including a HTML text file with 53,400 words, 11 JPG images and 1 JavaScript program) into 10-12 gram (1 picogram) of DNAs; and a new "bit-base" encoding method was also reported in this research for corresponding a bit (0-1 code) to a base, making it possible to store large multimedia files through DNA, however the error rate of this encoding method is relatively high, incorporated herein by reference. Almost at the same time, in 2013, Nick Goldman's research group from the European Bioinformatics Institute (EBI) reported their new research results of DNA storage in the journal Nature, and they succeeded to realize the DNA storage of ASCII, PDF, JPG and MP3 files, and first introduced a new error correction method for achieving 100% decoding and restoration of the above-mentioned files, incorporated herein by reference.

Since 2015, with the improvement of high-throughput DNA synthesis and sequencing technologies, the cost of DNA synthesis and sequencing was continued to decline, and the research on DNA storage also reached a new climax. In 2016, Blawat et al. cooperated with George Church's research group developed a new error correction method of DNA storage based on channel model, which can handle all types of errors during DNA synthesis, amplification and sequencing such as insertion, deletion, and recombination errors, and they successfully stored and retrieved 22M data with an accuracy rate of 100%, incorporated herein by reference. In 2017, in the journal *Science*, Yaniv Erlich's research group from Columbia University in the United States reported a novel DNA storage method based on the fountain code, which realized the storage of 2.15M multimedia files such as videos; compared with previous encoding methods, this method reduces the degree of redundancy through eliminating the overlaps for sequencing assembly, and increases the storage capacity by 60%, incorporated herein by reference.

In view of huge potential of DNA storage technology in future, the Microsoft Corporation of the United States had successively invested nearly 100 million U.S. dollars and cooperated with the James Bornholt's research group from the University of Washington to release a new DNA storage system that supports random-access reading of data in 2016. This system adopts a key-value mode addressing method, in which the storage address is divided into high and low parts, thereby increasing the flexibility of random-access reading. It succeed to realize the random-access reading of 42 kb subset data. Using the above-mentioned DNA storage system, the Microsoft Corporation had completed the DNA storage of about 200 MB of data by March 2018, including 100 classic literary works in the Gutenberg Project database, creating a new record in the field of DNA storage at the time.

Although DNA storage technology has many advantages over traditional data storage technologies, and relevant researches have made considerable progress in recent years, it has some disadvantages, mainly in two aspects. First, compared with traditional data storage technologies, its costing is very high, and the storage and reading are also very time-consuming, which greatly limit its practical application. Specifically, most design ideas of the above-mentioned DNA storage technologies are more similar to "engraving printing": for each DNA stored file, it is necessary to synthesize all sequences of fragments encoding DNA storage file, but these synthesized DNA fragments cannot be reused, thereby leading to a main disadvantage of high cost for DNA storage technology. Secondly, since many current DNA storage technologies are prone to generate some errors during synthesizing and sequencing of DNA sequences, a large amount of redundant DNA fragments are required for error correction, thereby resulting in additionally costs.

SUMMARY

In order to solve or at least partially solve the above technical problems, the disclosure is based on the concept of "movable type printing", one of the four great inventions of ancient China, and to one-to-one map a "DNA movable type unit" to corresponding data "payload movable type elements" (characters, pixels, audio amplitudes, etc.) and data "index movable type elements" (locations, file attributes, etc.), thereby realizing encoding, storage and precise decoding of quaternary DNA stored data (such as texts, pictures, audios, and videos). Specifically, the disclosure comprises the following aspects.

In a first aspect of the disclosure, provided herein is a method for DNA movable type storage, comprising:

(1) providing a physical library of data payload movable type elements and a physical library of index movable type elements, in which the payload movable type element library consists of a variety of oligonucleotides of data payload movable type elements (first oligonucleotides) that corresponds to various binary payload data information; the index movable type element library consists of a variety of oligonucleotides of index movable type elements (second oligonucleotides) that corresponds to various binary index data information;

(2) dividing the stored 0-1 binary data into corresponding data payload and index movable type elements; mapping the abovementioned data payload and index movable type elements to corresponding oligonucleotides from the physical libraries of data payload and index movable type elements, based on a codebook for encoding and decoding mapping rule between 0-1 binary codes and DNA A-T-C-G quaternary codes;

(3) linking the oligonucleotides of data payload movable type elements and the oligonucleotides of index movable type elements in step (2) to form a DNA movable type unit corresponding to a data element information, and all DNA movable type units form a DNA storage library that holds all the data element information of a stored file; and (4) sequencing the oligonucleotides from the DNA storage library in step (3), and decoding the sequencing results into binary stored data according to a codebook of data payload and index movable types using a corresponding decoding software.

In some embodiments, the stored data are selected from at least one of text data, image data, audio data and video data.

In some embodiments, the data payload movable type element is selected from at least one of a character, a pixel, an audio amplitude and a video frame; the index movable type elements comprises location and attribute information for a data payload element.

In some embodiments, the location information of the data payload movable type element comprises information of page number, row and column.

In some embodiments, the attribute information comprises file type, file name, file size, and creation time for the data payload element.

In some embodiments, the linker sequences are comprised in the oligonucleotides of data payload and index movable type elements in the DNA movable type units.

In some embodiments, the linker sequence is an overlapping reverse complement sequence or an enzymatically cleavable sequence.

In the second aspect of the disclosure provided herein is a system for DNA movable type storage, comprising:

a. a physical library of data payload movable type elements and a physical oligonucleotide library of index movable type elements: the physical library of data payload movable type elements consists of a variety of oligonucleotides of data payload movable type elements, each of which corresponds to a only data payload movable type element for the DNA stored file; and the physical library of index movable type elements consists of a variety of oligonucleotides of index movable type elements, each of which corresponds to a only index element;

b. an encoding module/software first provides for dividing the binary targeted stored data file into corresponding data payload and index movable type elements; and for each data payload movable type element and its index movable type elements, encoding module/software can achieve the transcoding from 0-1 binary codes to DNA A-T-C-G quaternary codes based on certain codebook/ mapping rule; these DNA A-T-C-G quaternary codes correspond to certain oligonucleotides from the physical libraries of payload and index movable type elements; and c. a decoding module/software provides for the transcoding from DNA A-T-C-G quaternary codes to 0-1 binary codes based on certain codebook/mapping rule using the decoding sequencing data of the DNA oligonucleotide stored data file.

In some embodiments, the system for DNA movable type storage further comprises related system for DNA linkers and related system for DNA sequencing.

BRIEF DESCRIPTION OF THE DRAWINGS

FIG. 4 is a design diagram of oligonucleotide sequences from an exemplary physical library of DNA movable types.

FIG. 5 is a mapping exemplary schematic diagram between 256 bytes and corresponding DNA sequences.

FIG. 6 is a flowchart of an exemplary encoding algorithm.

DETAILED DESCRIPTION

Various exemplary implementations in the disclosure are now described in detail. The detailed description should not be considered as a limitation on the invention, but should be understood as a more detailed description of certain aspects, characteristics, and embodiments of the disclosure.

It should be understood that the terms described in the disclosure are only used to describe specific implementations, rather than to limit the invention. In addition, for the numerical ranges in the disclosure, it should be understood that the upper limit and the lower limit of the range and each intermediate value between them are specifically disclosed. Each smaller range between an intermediate value among any stated values or within any stated range and an intermediate value among any other stated values or within any other stated range is also encompassed in the disclosure. The upper and lower limits of these smaller ranges can be independently included or excluded from the range.

Unless otherwise specified, all technical and scientific terms used herein have the same meaning as commonly understood by those of ordinary skill in the art to which the disclosure belongs. Although the disclosure only describes some methods and materials, any methods and materials similar or equivalent to those described herein can also be used in the implementation or testing of the disclosure. All documents mentioned in this specification are incorporated by reference to disclose and describe methods and/or materials related to the documents. In the event of conflict with any incorporated document, the description in this specification shall prevail. Unless otherwise specified, "%" is a percentage based on weight.

Method for DNA Movable Type Storage

In the first aspect of the disclosure, provided herein is a method for DNA movable type storage. The concept of DNA movable type is core and focus for the method of the disclosure, which is based on the synthesis, usage of various DNA sequences and their combinations to achieve DNA data encoding, storage, and decoding/precise-interpretation, therefore, it can also be referred to as a "method for storing data using artificially synthesized DNAs", or a "method for storing data using base sequences".

Figure 1:
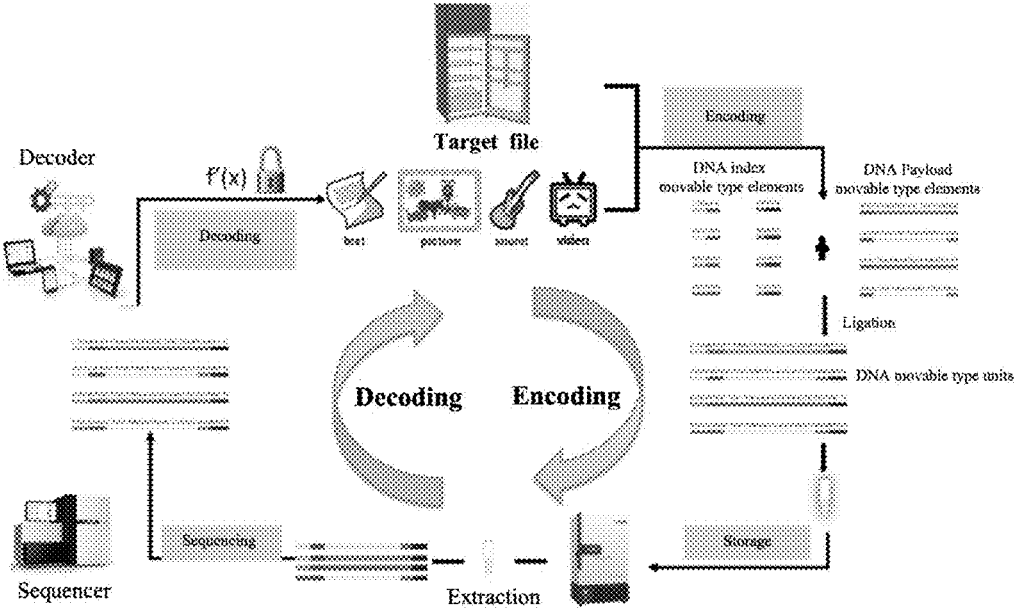
FIG. 1 is a schematic diagram of an exemplary system for DNA movable type storage.

FIG. 1 shows an example of a DNA movable type storage method and system. The storage method of the disclosure at least comprising:

(1) providing a physical library of data payload movable type elements and a physical library of index movable type elements, wherein the physical library of data payload movable type elements consists of a variety of oligonucleotides of data payload movable type elements which are stored separately, and each of them corresponds to different data payload elements for DNA data storage; and the physical library of index movable type consists of a variety of oligonucleotides of index movable type elements which are stored separately, and each of them corresponds to different index element;

(2) dividing the stored 0-1 binary data into corresponding data payload and index movable type elements; mapping the abovementioned data payload and index movable type elements to corresponding oligonucleotides from the physical libraries of data payload and index movable type elements, based on a codebook for encoding and decoding mapping rule between 0-1 binary codes and DNA A-T-C-G quaternary codes;

(3) linking the oligonucleotides of data payload movable type elements and the oligonucleotides of index movable type elements in step (2) to form a DNA movable type unit, and all DNA movable type units to form a DNA storage library that holds all the data element information of a stored file; and (4) sequencing the oligonucleotides from the DNA storage file in step (3), and decoding the sequencing results into binary stored data according to a codebook of the data payload and index movable types using a corresponding decoding software.

Step (1)

In the disclosure, step (1) is a step of providing a physical library of data payload movable type elements and a physical library of index movable type elements. This step comprises constructing such physical libraries or using existing physical library. The physical library refers to a library composed of many different types of oligonucleotides, and usually each type of oligonucleotide is stored separately or independently. For the convenience of illustration, these oligonucleotides that constitute the physical library of data payload movable type elements are referred to as the oligonucleotides of data payload movable type elements (first oligonucleotides). The oligonucleotides that constitute the physical library of index movable type elements are referred to as the oligonucleotides of index movable type (second oligonucleotides). Either the oligonucleotides of data payload and index movable type elements can be single-stranded or double-stranded DNAs.

In the disclosure, the oligonucleotides of data payload movable type elements are of multiple different types, each type is stored separately, and each type of DNA sequences uniquely correspond to the data payload elements of the stored data file. Similarly, there are also many different types of oligonucleotides for index movable type elements, and each type is also stored separately. Each index movable type of DNA sequences corresponds to different levels of index information respectively. The oligonucleotide sequences are generated from permutations and combinations of four different bases (A, T, C, and G). The longer the sequence, the more permutations and combinations are obtained, and thus the more oligonucleotide types are obtained. Therefore, the desired oligonucleotide types/classes can be obtained by manipulating the length of oligonucleotides, thereby achieving the one-to-one correspondence between the oligonucleotides of data payload movable type elements and numerous data elements, or the one-to-one correspondence between the oligonucleotides of index movable type and a large amount of different index information.

In the case of no available physical library, step (1) of the disclosure also comprises reconstructing a physical library of data payload movable type elements and a physical library of index movable type elements. In an exemplary construction method, the quaternary encoding method using specific permutations and combinations of four kinds of bases (A, T, C and G) is used to create the libraries for the indicated data payload and index movable type elements. As shown in FIG. 4, the method comprises the following steps:

A set of DNA sequence combination is obtained by randomly permuting and combining the "A, T, C and G", and then the dirty sequences in the set are cleaned up to obtain a library of candidate sequences. In some embodiments, the dirty sequences mainly comprise some sequences that can affect the sequencing and PCR effects, such as repeat sequences, palindrome sequences, higher structure-forming sequences, high GC content (>65%) sequences, and single continuous repeat bases (>3nt)-containing sequences. The oligonucleotides in the library of candidate sequences are then synthesized, used as the physical libraries (comprising a library of data payload movable type and a library of index movable type elements), and stored at −80° C. in a refrigerator.

FIG. 5 shows an example, in which the library of data payload of movable type elements is composed of 256 DNA sequences, and each sequence represents one byte data payload in a binary file.

Step (2)

In the disclosure, the step (2) is an encoding step, comprising dividing and annotating of the stored data, and generating a one-to-one correspondence between the binary data and the quaternary oligonucleotides in the physical libraries. Specifically, the binary data of the stored target file is first divided into a plurality of data payload movable type elements, and each data payload movable type element is then annotated with corresponding index movable type element information; for the data payload and index movable type elements in each data movable type unit, the encoding module/software can achieve the transcoding from 0-1 binary codes to DNA A-T-C-G quaternary codes based on certain mapping rule/codebook; corresponding oligonucleotides are finally obtained from the physical libraries of data payload and index movable type elements.

In the disclosure, the stored data is any known type of data, which includes, but is not limited to, text data, image data, audio data, and video data. The stored data in the disclosure may be at least one of the above-mentioned data. In a specific embodiment, the stored data is text data.

In the disclosure, a data payload or index movable type element is generally a minimum/repeat element of stored file, examples of which include, but are not limited to, characters, pixels, audio amplitudes, and video frames. At least one of the above-mentioned examples can be used in the disclosure. Preferably, the data element is a element repeated multiple times in the stored data. For example, in Chinese text data, the data element may be either individual Chinese character, such as "我", "的", and "人", or expression or phrase composed of Chinese characters, such as "我们", "中国", "伟大", and "勤劳勇敢". The data element may also comprise punctuation marks, such as comma, full stop, space, and the like. As another example, in English text data, the data elements can be either English words, such as "hello" and "world", or may be single English letters, such as "A", "a", "Y", etc. When the data element is phrase, the commonly used phrases with higher repetitions are preferred.

In the disclosure, the index elements comprise location and attribute information of a data payload movable type element in the stored file. For example, the location information of the data payload element comprises information of page number, row and column. As another example, the attribute information of a file comprises file type, file name, file size, creation time and the like. Generally, each data payload movable type element needs to be annotated with multiple levels of or multiple index element information.

In the step (2) of the disclosure, the one-to-one correspondence between the data payload movable type element and oligonucleotide is realized through an association table (codebook) of data payload movable type, and the one-to-one correspondence between the index movable type information and oligonucleotide is realized through an association table of index movable type.

In exemplary embodiments, the encoding in step (2) is based on a codebook/association table (comprising a codebook/association table of data payload movable type and a codebook/association table of index movable type), and using an encoding software to convert each binary data element in a target file to corresponding oligonucleotide combination or a data payload movable type element and relate index movable type elements. As for the encoding software, it is for example written in a programming language such as Python, Java, so as to achieve the purpose of dividing and encoding the DNA movable type unit of the target file. An algorithm process of encoding software is shown in FIG. 6, and the details are as follows: dividing each movable type unit of a target file into corresponding data payload movable type and index movable type elements, according to an association table/codebook of the data payload movable type and an association table of the index movable type, thereby achieving the coding of data payload movable type and index movable type elements for the target file. It provides a guidance for the subsequent formation of each DNA movable type unit of the target file through linkage or PCR experiments.

Step (3)

The step (3) of the disclosure is a step for DNA movable type storage, which specifically comprises the linkage of oligonucleotides of the data payload and index movable type elements in step (2) to form a DNA movable type unit corresponding to each data element, and allowing a plurality of DNA movable type units to form a storage library that holds all the stored data.

Figure 2:
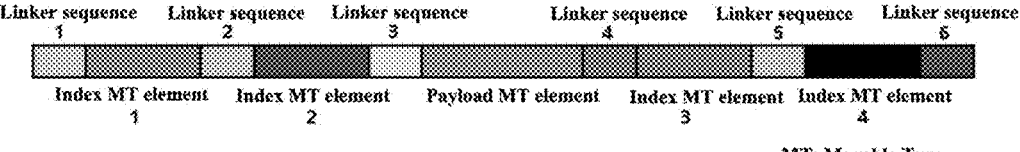
FIG. 2 is a schematic diagram of the structure of an exemplary DNA movable type unit.
Figure 3:
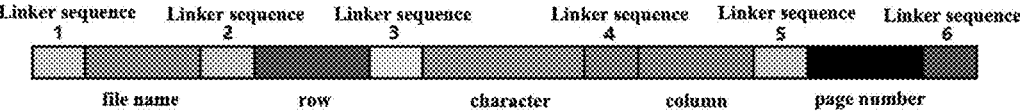
FIG. 3 is a schematic diagram of the structure of an exemplary DNA movable type unit of text file.

In the disclosure, the storage library comprises a large number of DNA movable type units, each DNA movable type unit is a oligonucleotide, and each oligonucleotide is a linked sequence of a plurality of single-stranded or double-stranded DNA sequences composed of specific permutations and combinations of four bases (A, T, C and G), which corresponds or maps to data payload and index movable type elements. Such multiple mapping relationship forms a two-way correspondence between a codebook/association table of data payload movable type and a codebook/association table of index movable type. In some embodiments, a library of DNA movable type storage file in the disclosure comprises a plurality of DNA movable type units, and each DNA movable type unit comprises a oligonucleotide with data payload and index movable type elements (as shown in FIG. 2 and FIG. 3). The number of the index movable type elements is not particularly limited, and for example, it is an even number, such as 2, 4, 6, 8 and other even number of sequences of index movable type elements.

In the DNA movable type unit of the disclosure, a linker sequence exists among the oligonucleotides of data payload and index movable type elements. The linker sequence is located at one/both end of an oligonucleotide sequence, for example, forming a combination of linker-payload-index oligonucleotide sequences. The purpose of the linker sequence is to realize the linking and assembling of the data payload movable type and the index movable type elements into a DNA movable type unit. The number of linker sequences is not particularly limited, and for example it is a natural number such as 1, 2, 3, 4, 5, 6, 7 and 8 linker sequences. In some embodiments, these linker sequences are PCR primer sequences or enzymatically cleavable linkers. In some specific embodiments, the linkage of these linker sequences for the abovementioned oligonucleotides are achieved by polymerase chain reaction.

In some exemplary embodiments, the method of the disclosure comprises converting the binary data in the target file to a A-T-C-G quaternary file composed of DNA movable type units by encoding software, and then obtaining the corresponding DNA movable type elements from physical libraries of data payload movable type and index movable type elements. In some specific embodiments, PCR, linkage and other reactions can be used to link the data and index payload movable type elements to form each DNA movable type unit of the target file, and finally the various DNA movable type units are collected and cryopreserved to complete the DNA movable type storage of a target file. In order to store each movable type unit for a long time and used repeatedly for many times, preferably, each movable type unit may be cloned into a plasmid and introduced into *Escherichia coli* for preservation to achieve this purpose. The plasmid and *Escherichia coli* are not particularly limited. In some specific embodiments, each movable type unit is cloned into a PUC19 plasmid and introduced into *Escherichia coli* DH5α for preservation.

Step (4)

The step (4) is a decoding step, which is an optional step in the method for DNA movable type storage. The decoding step generally comprises the step of sequencing the oligonucleotides in the storage library. In some embodiments, firstly, using for example a high-throughput sequencing platform to sequence the DNA sequences of a DNA movable type storage file to obtain all the sequence information of the DNA oligonucleotides of the target file at one time; then using a decoding software to decode the DNA sequences of the binary target file, and output a readable target file to realize information decoding and precise interpretation of the DNA movable type oligonucleotides. The decoding step can decode the sequencing result into the binary data of stored file, based on the association table/codebook of data payload and index movable type elements.

System for DNA Movable Type Storage

In a second aspect of the disclosure, provided herein is a system for DNA movable type storage, at least comprising the following items (a~c):

a. physical libraries of oligonucleotides comprise a physical library of data payload movable type elements and a physical library of index movable type elements, wherein the physical library of data payload movable type elements consists of a variety of oligonucleotides of data payload movable type elements which stored separately, and each oligonucleotide sequence corresponds to one data payload element in the targeted data file; and the physical library of index movable type elements consists of a variety of oligonucleotides of index movable type elements which stored separately, and each oligonucleotide base sequence corresponds to different index movable type element respectively;

b. an encoding module/software which provided for dividing the stored data of a target file into a plurality of data movable type units, which contained certain data payload movable type elements with annotating index data movable type elements; based on an encoding software from association table/codebook, the binary data of movable type units were transcoded into corresponding oligonucleotide base sequences in the physical libraries of data payload and index movable type elements; and c. a decoding module/software which provided for decoding the sequencing data of the oligonucleotides in the storage library into the binary stored data in a target file according to an association table of the data payload/index movable type elements and a corresponding decoding software.

The physical library of data payload movable type elements and the physical library of index movable type elements in the disclosure contains series of different oligonucleotides which stored separately. In certain embodiments, the physical library data payload movable type elements is stored in a series of containers (e.g., test tubes, EP tubes): one sequence of oligonucleotide of data payload movable type element is stored in a container, and one sequence of oligonucleotide uniquely corresponds to one data payload movable type element. Similarly, the physical library of index movable type elements is also stored in a series of containers (e.g., test tubes, EP tubes): one sequence of oligonucleotide of index movable type element is stored in a container, and the sequence of oligonucleotide uniquely corresponds to one data index movable type element. The oligonucleotides in different containers are quantitatively added into the DNA linking reaction system according to the encoding result.

The oligonucleotide physical libraries of the disclosure (comprising the physical library of data payload movable type elements, the physical library of index movable type elements and the physical library of linkers) are in a solution or dry powder state in which a specified amount of oligonucleotides are comprised. Typically, the oligonucleotide physical libraries are stored at a low temperature such as −80° C. Different physical libraries are used in solution state, which can be called by, for example, automatic machine manipulation.

Figure 7:
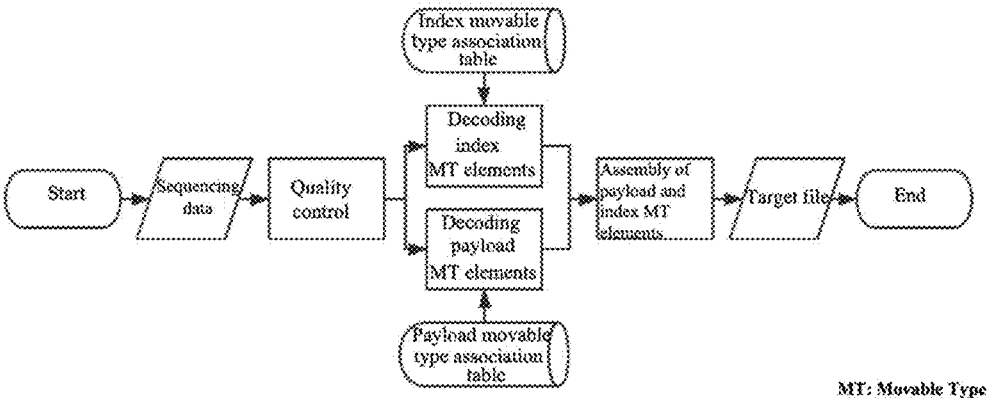
FIG. 7 is a flowchart of an exemplary decoding algorithm.

The encoding module and decoding module of the disclosure are typically implemented by software(s). As an exemplary software, it specifically implements the task of converting binary data files of various formats into quaternary DNA sequence information. In some embodiments, the encoding software is written in program languages such as Python and Java, to achieve the goal of dividing and encoding a binary data target file into DNA movable type units, with an algorithm process as shown in FIG. 6. In the decoding module, it typically implements the task of converting the DNA movable type sequence data obtained through high-throughput sequencing into a readable binary data target file, wherein the target file here may be texts, images, audios, videos. In some embodiments, the decoding software typically comprises multiple sub-modules such as a sub-module for controlling DNA sequence quality, a sub-module for decoding data payload movable type elements, a sub-module for decoding index movable type elements, and a sub-module for outputting binary data target file, which are integrated into a data decoding module (as shown in FIG. 7), to achieve the decoding and precise interpretation of the DNA oligonucleotide sequences into the binary data target file.

Optionally, the system for DNA movable type storage of the disclosure further comprises at least one of a system for linking DNA, a system for sequencing DNA, and a system for DNA cryogenic storage.

The system for linking DNAs of the disclosure refers to a system for linking at least two oligonucleotides, and generally speaking, it comprises a reaction container, various reaction reagents and a controller. There may be one or more reaction container. For example, the reaction container is an EP tube. The various reaction reagents of the disclosure comprise a buffer and DNA ligase. Known commercial reaction reagents can be used in the disclosure. The controller of the disclosure is an instrument for controlling reaction conditions such as 37° C.

The system for DNA sequencing of the disclosure can be any known commercial system, for example, a second-generation sequencing system (i.e., the next-generation sequencing technology) including Illumina sequencers. The DNA sequencing system of the disclosure can also be a third-generation sequencing system (i.e., a single-molecule sequencing system), such as Pacbio or Oxford nanopore sequencing platforms.

The system for DNA cryogenic storage of the disclosure refers to a system for long-term storage of oligonucleotides. Known commercial systems can be used. Generally speaking, DNA can be stored at a low temperature for at least 50 years, preferably at least 100 years, and more preferably not less than 200 years. The cryogenic storage system comprises a cryogenic refrigerator.

In the system for DNA movable type storage of the disclosure, each subsystem or component can either be a separated part, which can be combined into a complete system when in use, or be integrated into a whole; and each subsystem or component can be controlled by a controller as a whole to achieve coordinated operation, thereby realizing the automatic encoding, storage or decoding of DNA stored data.

EXAMPLES

DNA movable type storage of a classical Chinese poem by Li Bai, *行路难 · 其一*, "长风破浪会有时, 直挂云帆济沧海。" was used as an example of the disclosure, and the PCR method was used for linking.

1. Encoding and Synthesis of DNA Sequences of DNA Movable Type Units

According to the method of the disclosure, a file composed of movable type units was designed and used to generate for "长风破浪会有时, 直挂云帆济沧海。", as shown in Table 1. According to this file, with the help of the encoding software, the DNA sequences of 12 bp data payload movable type elements as shown in Table 2 and the sequences of 8 bp index movable type elements as shown in Table 3 were generated, and the corresponding DNA sequences were synthesized.

TABLE 1

| File composed of movable type units | | | | |
|---|---|---|---|---|
| File name | Row | Movable type element | Column | Page |
| 行路难 · 其一 | 8 | 长 | 1 | 1 |
| 行路难 · 其一 | 8 | 风 | 2 | 1 |
| 行路难 · 其一 | 8 | 破 | 3 | 1 |
| 行路难 · 其一 | 8 | 浪 | 4 | 1 |
| 行路难 · 其一 | 8 | 会 | 5 | 1 |
| 行路难 · 其一 | 8 | 有 | 6 | 1 |
| 行路难 · 其一 | 8 | 时 | 7 | 1 |
| 行路难 · 其一 | 8 | , | 8 | 1 |
| 行路难 · 其一 | 8 | 直 | 9 | 1 |
| 行路难 · 其一 | 8 | 挂 | 10 | 1 |
| 行路难 · 其一 | 8 | 云 | 11 | 1 |
| 行路难 · 其一 | 8 | 帆 | 12 | 1 |
| 行路难 · 其一 | 8 | 济 | 13 | 1 |
| 行路难 · 其一 | 8 | 沧 | 14 | 1 |
| 行路难 · 其一 | 8 | 海 | 15 | 1 |
| 行路难 · 其一 | 8 | 。 | 16 | 1 |

TABLE 2

| Sequences of data payload movable type elements of the target file | | | |
|---|---|---|---|
| Payload information | Linker sequence on the left side | Payload movable type element | Linker sequence on the right side |
| 长 | ATAAGCCTCGAGTAG | GCGTAGCTGTAC | TGATAGTACCAGAGC |
| 风 | ATAAGCCTCGAGTAG | GCAGGACACTGT | TGATAGTACCAGAGC |
| 破 | ATAAGCCTCGAGTAG | DACGGTCAAGTG | TGATAGTACCAGAGC |
| 浪 | ATAAGCCTCGAGTAG | TGCGCATGACAG | TGATAGTACCAGAGC |
| 会 | ATAAGCCTCGAGTAG | ACTAATACGTCG | TGATAGTACCAGAGC |
| 有 | ATAAGCCTCGAGTAG | CTACCGACTCTG | TGATAGTACCAGAGC |
| 时 | ATAAGCCTCGAGTAG | TCTCACAGTAGC | TGATAGTACCAGAGC |
| , | ATAAGCCTCGAGTAG | CACGGTCTCGAT | TGATAGTACCAGAGC |
| 直 | ATAAGCCTCGAGTAG | TCACCACTTCTA | TGATAGTACCAGAGC |
| 挂 | ATAAGCCTCGAGTAG | AGCTCACAGCGT | TGATAGTACCAGAGC |
| 云 | ATAAGCCTCGAGTAG | CGAGGATCACAC | TGATAGTACCAGAGC |
| 帆 | ATAAGCCTCGAGTAG | AGCTTGACGTAT | TGATAGTACCAGAGC |
| 济 | ATAAGCCTCGAGTAG | TGAGTCAGACAT | TGATAGTACCAGAGC |
| 沧 | ATAAGCCTCGAGTAG | TAGTACTGTCGC | TGATAGTACCAGAGC |
| 海 | ATAAGCCTCGAGTAG | TGTGCTATCACT | TGATAGTACCAGAGC |
| 。 | ATAAGCCTCGAGTAG | CACACATCTAGT | TGATAGTACCAGAGC |

TABLE 3

| Sequences of index movable type elements of the target file | | | |
| --- | --- | --- | --- |
| Index information | Linker sequence on the left side | Index movable type element | Linker sequence on the right side |
| 行路难・其一 | AGCTATACGGAGCAT | CGTGAGAT | TAGTCAACTAGCCTC |
| Page 1 | CTACATGTCCAGGCA | ATGCCGTA | GCTTGTGACAGCATA |
| Row 8 | TAGTCAACTAGCCTC | GTCATCGT | ATAAGCCTCGAGTAG |
| Column 1 | TGATAGTACCAGAGC | CAGAACGA | CTACATGTCCAGGCA |
| Column 2 | TGATAGTACCAGAGC | AGCATCGA | CTACATGTCCAGGCA |
| Column 3 | TGATAGTACCAGAGC | TGATGCTG | CTACATGTCCAGGCA |
| Column 4 | TGATAGTACCAGAGC | GATCCTGA | CTACATGTCCAGGCA |
| Column 5 | TGATAGTACCAGAGC | ACATCGCT | CTACATGTCCAGGCA |
| Column 6 | TGATAGTACCAGAGC | GATGAGTG | CTACATGTCCAGGCA |
| Column 7 | TGATAGTACCAGAGC | AGCTTCAG | CTACATGTCCAGGCA |
| Column 8 | TGATAGTACCAGAGC | CTAGCTCA | CTACATGTCCAGGCA |
| Column 9 | TGATAGTACCAGAGC | CTACACAG | CTACATGTCCAGGCA |
| Column 10 | TGATAGTACCAGAGC | TAGCCACT | CTACATGTCCAGGCA |
| Column 11 | TGATAGTACCAGAGC | AGTGATGC | CTACATGTCCAGGCA |
| Column 12 | TGATAGTACCAGAGC | CATCATGC | CTACATGTCCAGGCA |
| Column 13 | TGATAGTACCAGAGC | TGCAACGT | CTACATGTCCAGGCA |
| Column 14 | TGATAGTACCAGAGC | ACGCATCA | CTACATGTCCAGGCA |
| Column 15 | TGATAGTACCAGAGC | GTGATGCT | CTACATGTCCAGGCA |
| Column 16 | TGATAGTACCAGAGC | TGACCTAG | CTACATGTCCAGGCA |

The synthesized DNA sequences of data payload movable type elements were diluted to 0.01 μM, and the synthesized sequences of row, column and page index movable type elements were diluted to 5 μM.

2. Assembly of the Data Payload Movable Type Elements and the Corresponding Index Movable Type Elements by PCR to Form DNA Movable Type Units According to the guidance file of Table 2, each movable type unit was formed by PCR linking as per the structure of "file name-row-data payload movable type-column-page", and the components therein were assembled together by PCR using linker sequences between two components. The specific process was as follows:

2.1 Assembly of the Movable Type Unit with the Structure of "File Name-Row-Data Payload Movable Type-Column-Page"

The first step of assembly: a unit of "row-data payload movable type-column" was assembled. PCR reaction system: 5 μl of 2×Es Taq MasterMix, 1 μl of each of the diluted movable type, row and column oligos, and 2 μl of sterile water. Pre-denaturation at 94° C. for 2 min; then denaturation at 94° C. for 30 s, annealing at 62° C. for 30 s, and extension at 72° C. for 30 s, 30 cycles; and finally, extension at 72° C. for 2 min.

The second step of assembly: the unit of "row-data payload movable type-column" formed in the first step was secondly assembled with the file name and page number to form a DNA movable type unit of "file name-row-data payload movable type-column-page". PCR reaction system: 25 μl of 2×Es Taq MasterMix, 1 μl of unit of "row-movable type-column", 10 μl of each of diluted file name and page number oligos, and 4 μl of sterile water. Pre-denaturation at 94° C. for 2 min; then denaturation at 94° C. for 30 s, annealing at 62° C. for 30 s, and extension at 72° C. for 30 s, 30 cycles; and final extension at 72° C. for 2 min.

2.2 Purification of the Complete DNA Movable Type Unit of "File Name-Row-Data Payload Movable Type-Column-Page"

Figure 8:
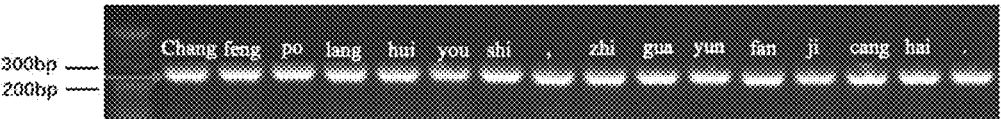
FIG. 8 shows all movable type units generated by PCR in an exemplary target text file.

The movable type units assembled in the second step were separated by 2% agarose gel electrophoresis (electrophoresis was run at a voltage of 90 V for 35 minutes), and the target fragments were cut off, recovered and purified using Zymoclean Gel DNA Recovery Kit. Each of the movable type units of "file name-row-data payload movable type-column-page" was shown by the arrow in FIG. 8.

3. DNA Movable Type Storage of a Target Text File

In order to store each movable type unit for a long time and use it repeatedly, we cloned each movable type unit into PUC19 plasmid and introduced it into *E. coli* DH5α for storage. The specific process was as follows:

3.1 Enzymatic Digestion

Each purified movable type unit and pUC19 plasmid were quantified with Nanodrop, and digested with enzymes EcoRI and XbaI. Enzymatic digestion system: 1 μl of 10×NEB 2.1 buffer, 0.5 μl of EcoRI (NEB), 0.5 μl of XbaI (NEB), 500 ng of pUC19 and 200 ng of movable type units, ddH$_2$O complemented to 10 μl, digestion at 37° C. for 1 h.

3.2 Enzymatic Ligation

Each movable type unit and plasmid which had been subjected to the enzymatic digestion in the previous step were quantified with Nanodrop, and mixed in a ratio of 1:2, 10 μl mixture was taken out, 2 μl of 10×T4 DNA ligase buffer, 1 μl of T4 DNA ligase and 7 μl of ddH$_2$O were added, and ligated overnight at 16° C.

3.3 Transformation

The enzymatic ligation product from the previous step was added to 100 μl of DH5α, placed on ice for 30 min, heat shocked at 42° C. for 90 s, quickly placed on ice for 3 min, added to 500 μl of LB medium and cultured at 37° C. at 200 rpm for 1 h, and 100 μl of the resultant was taken and spread on an ampicillin resistant LB plate, and cultured overnight at 37° C. The colonies on the plate were picked up for Sanger sequencing verification. The validated successful clone for each Chinese character was selected, cultured in an LB medium to the logarithmic phase, and stored in 30% glycerol at −80° C. for a long time.

4. Decoding

Figure 9:
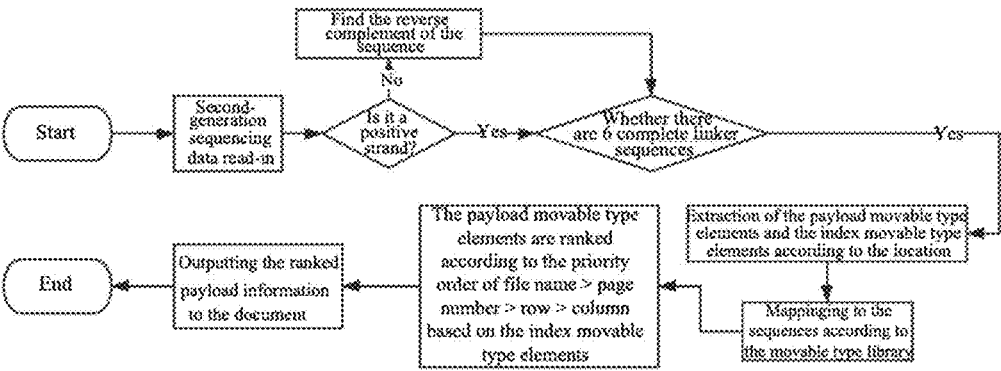
FIG. 9 is a flowchart of an exemplary decoding algorithm of a text file.
Figure 10:
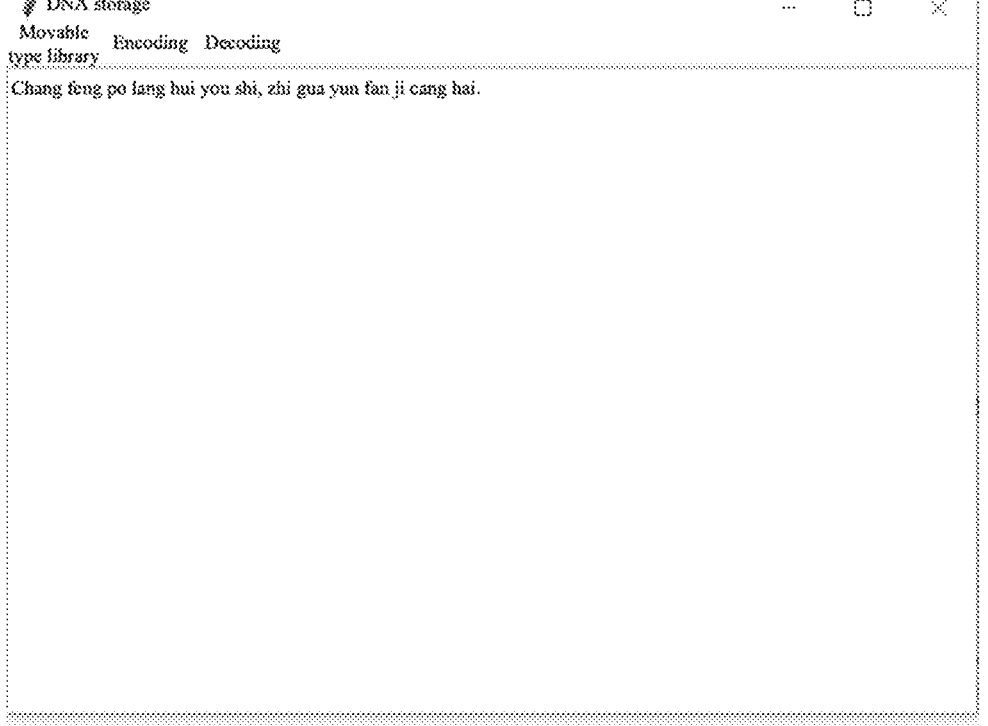
FIG. 10 is a diagram showing an exemplary software decoding result.

The storage files with 16 DNA movable type unit for "长风破浪会有时，直挂云帆济沧海。" were taken out from the refrigerator, thawed, and amplified. The decoding libraries for second-generation sequencing were then constructed, sequenced using illumina Hiseq4000 sequencing platform, and decoded with the decoding software. The specific text file decoding algorithm process was shown in FIG. 9, where the index movable type elements were ranked according to the priority order of file name>page number>row>column. The output target file is as shown in FIG. 10.

Similarly, the full text of 行路难·其 · by Li Bai can be encoded. For details, please refer to the whole poem and the position encoding table.

行路难·其一

【作者】李白【朝代】唐

金樽清酒斗十千，玉盘珍羞直万钱。

停杯投箸不能食，拔剑四顾心茫然。

欲渡黄河冰塞川，将登太行雪满山。

闲来垂钓碧溪上，忽复乘舟梦日边。

行路难！行路难！多歧路，今安在？

长风破浪会有时，直挂云帆济沧海。

| | |
|---|---|
| 1 行 column 1<br>row 1 page 1 行路难.txt | AGCTATACGGAGCATCGTGAGATTAGTCAACTAGCCTCACACATGCATA<br>AGCCTCGAGTAGCGACGAGCCATATGATAGTACCAGAGCCAGAACGAC<br>TACATGTCCAGGCAATGCCGTAGCTTGTGACAGCATA |
| 2 路<br>column 2<br>row 1 page 行路难.txt | AGCTATACGGAGCATCGTGAGATTAGTCAACTAGCCTCACACATGCATA<br>AGCCTCGAGTAGCTCAGATGGCATTGATAGTACCAGAGCAGCATCGAC<br>TACATGTCCAGGCAATGCCGTAGCTTGTGACAGCATA |
| 3 难 column 3<br>row 1 page 1<br>行路难.txt | AGCTATACGGAGCATCGTGAGATTAGTCAACTAGCCTCACACATGCATA<br>AGCCTCGAGTAGACTCTAGTGTGATGATAGTACCAGAGCTGATGCTGCT<br>ACATGTCCAGGCAATGCCGTAGCTTGTGACAGCATA |
| 4 行路 column 4<br>Row 1 page 1<br>难.txt | AGCTATACGGAGCATCGTGAGATTAGTCAACTAGCCTCACACATGCATA<br>AGCCTCGAGTAGGATGGCGTGAGATGATAGTACCAGAGCGATCCTGAC<br>TACATGTCCAGGCAATGCCGTAGCTTGTGACAGCATA |
| 5 其 column 5<br>row 1 page 1<br>行路难.txt | AGCTATACGGAGCATCGTGAGATTAGTCAACTAGCCTCACACATGCATA<br>AGCCTCGAGTAGACAGCGACCTGATGATAGTACCAGAGCACATCGCTC<br>TACATGTCCAGGCAATGCCGTAGCTTGTGACAGCATA |
| 6 行路难 column 6<br>row 1 page 1<br>行路难.txt | AGCTATACGGAGCATCGTGAGATTAGTCAACTAGCCTCACACATGCATA<br>AGCCTCGAGTAGGTATCACGTGCGTGATAGTACCAGAGCGATGAGTGC<br>TACATGTCCAGGCAATGCCGTAGCTTGTGACAGCATA |
| 7 \n column 7 row<br>1 page 1 行路<br>难.txt | AGCTATACGGAGCATCGTGAGATTAGTCAACTAGCCTCACACATGCATA<br>AGCCTCGAGTAGGTCAACGCTCATTGATAGTACCAGAGCAGCTTCAGCT<br>ACATGTCCAGGCAATGCCGTAGCTTGTGACAGCATA |
| 8 【column 1<br>row 2 page 1<br>行路难.txt | AGCTATACGGAGCATCGTGAGATTAGTCAACTAGCCTCGCATGTGTATA<br>AGCCTCGAGTAGAGAGGTGACTCATGATAGTACCAGAGCCAGAACGAC<br>TACATGTCCAGGCAATGCCGTAGCTTGTGACAGCATA |
| 9 作 column<br>row 2 page 2<br>行路难.txt | AGCTATACGGAGCATCGTGAGATTAGTCAACTAGCCTCGCATGTGTATA<br>AGCCTCGAGTAGAGAGACACCATCTGATAGTACCAGAGCAGCATCGAC<br>TACATGTCCAGGCAATGCCGTAGCTTGTGACAGCATA |
| 10 者 column 3<br>row 2 page 1<br>行路难.txt | AGCTATACGGAGCATCGTGAGATTAGTCAACTAGCCTCGCATGTGTATA<br>AGCCTCGAGTAGTCTGATCGAGCATGATAGTACCAGAGCTGATGCTGCT<br>ACATGTCCAGGCAATGCCGTAGCTTGTGACAGCATA |

-continued

11 】column 4
row 2 page 1 行路
难.txt

AGCTATACGGAGCATCGTGAGATTAGTCAACTAGCCTCGCATGTGTATA
AGCCTCGAGTAGTATGGATCCGTATGATAGTACCAGAGCGATCCTGACT
ACATGTCCAGGCAATGCCGTAGCTTGTGACAGCATA

12 李 column 5
row 2 page 1
行路难.txt

AGCTATACGGAGCATCGTGAGATTAGTCAACTAGCCTCGCATGTGTATA
AGCCTCGAGTAGGACGTACGGAGATGATAGTACCAGAGCACATCGCTC
TACATGTCCAGGCAATGCCGTAGCTTGTGACAGCATA

13 白 column 6
row 2 page 1
行路难.txt

AGCTATACGGAGCATCGTGAGATTAGTCAACTAGCCTCGCATGTGTATA
AGCCTCGAGTAGGTACCACTATGTTGATAGTACCAGAGCGATGAGTGCT
ACATGTCCAGGCAATGCCGTAGCTTGTGACAGCATA

14 \0 column 7 row
2 page 1 行路
难.txt

AGCTATACGGAGCATCGTGAGATTAGTCAACTAGCCTCGCATGTGTATA
AGCCTCGAGTAGCTGCCACTCTACTGATAGTACCAGAGCAGCTTCAGCT
ACATGTCCAGGCAATGCCGTAGCTTGTGACAGCATA

15 【 column 8
row 2 page 1 行路难.txt

AGCTATACGGAGCATCGTGAGATTAGTCAACTAGCCTCGCATGTGTATA
AGCCTCGAGTAGAGAGGTGACTCATGATAGTACCAGAGCCTAGCTCAC
TACATGTCCAGGCAATGCCGTAGCTTGTGACAGCATA

16 朝 column 9
row 2 page 1 行路难.txt

AGCTATACGGAGCATCGTGAGATTAGTCAACTAGCCTCGCATGTGTATA
AGCCTCGAGTAGCACATGACAGATGATAGTACCAGAGCCTACACAGC
TACATGTCCAGGCAATGCCGTAGCTTGTGACAGCATA

17 代 column 10
row 2 page 1 行路难.txt

AGCTATACGGAGCATCGTGAGATTAGTCAACTAGCCTCGCATGTGTATA
AGCCTCGAGTAGTGAGCTCGATGTTGATAGTACCAGAGCTAGCCACTCT
ACATGTCCAGGCAATGCCGTAGCTTGTGACAGCATA

18 】column 11
row 2 page 1 行路难.txt

AGCTATACGGAGCATCGTGAGATTAGTCAACTAGCCTCGCATGTGTATA
AGCCTCGAGTAGTATGGATCCGTATGATAGTACCAGAGCAGTGATGCCT
ACATGTCCAGGCAATGCCGTAGCTTGTGACAGCATA

19 庚 column 12
row 2 page 1 行路难.txt

AGCTATACGGAGCATCGTGAGATTAGTCAACTAGCCTCGCATGTGTATA
AGCCTCGAGTAGGTGCACTGTCACTGATAGTACCAGAGCCATCATGCCT
ACATGTCCAGGCAATGCCGTAGCTTGTGACAGCATA

20 \n column 13
row 2 page 1 行路难.txt

AGCTATACGGAGCATCGTGAGATTAGTCAACTAGCCTCGCATGTGTATA
AGCCTCGAGTAGGTCAACGCTCATTGATAGTACCAGAGCTGCAACGTCT
ACATGTCCAGGCAATGCCGTAGCTTGTGACAGCATA

21 金 column 1
row 3 page 1 行路难.txt

AGCTATACGGAGCATCGTGAGATTAGTCAACTAGCCTCACACCTCTATA
AGCCTCGAGTAGGTCTATGACTCATGATAGTACCAGAGCCAGAACGAC
TACATGTCCAGGCAATGCCGTAGCTTGTGACAGCATA

22 樽 column 2
row 3 page 1 行路难.txt

AGCTATACGGAGCATCGTGAGATTAGTCAACTAGCCTCACACCTCTATA
AGCCTCGAGTAGCTAGCAGATCACTGATAGTACCAGAGCAGCATCGAC
TACATGTCCAGGCAATGCCGTAGCTTGTGACAGCATA

23 清 column 3
row 3 page 1 行路难.txt

AGCTATACGGAGCATCGTGAGATTAGTCAACTAGCCTCACACCTCTATA
AGCCTCGAGTAGTCTAGTAGGATCTGATAGTACCAGAGCTGATGCTGCT
ACATGTCCAGGCAATGCCGTAGCTTGTGACAGCATA

24 酒 column 4
row 3 page 1 行路难.txt

AGCTATACGGAGCATCGTGAGATTAGTCAACTAGCCTCACACCTCTATA
AGCCTCGAGTAGGATAAGCAGAGTTGATAGTACCAGAGCGATCCTGAC
TACATGTCCAGGCAATGCCGTAGCTTGTGACAGCATA

25 斗 column 5
row 3 page 1 行路难.txt

AGCTATACGGAGCATCGTGAGATTAGTCAACTAGCCTCACACCTCTATA
AGCCTCGAGTAGAGCACACACACTTGATAGTACCAGAGCACATCGCTCT
ACATGTCCAGGCAATGCCGTAGCTTGTGACAGCATA

26 十 column 6
row 3 page 1 行路难.txt

AGCTATACGGAGCATCGTGAGATTAGTCAACTAGCCTCACACCTCTATA
AGCCTCGAGTAGTCGTGTCGGCTATGATAGTACCAGAGCGATGAGTGCT
ACATGTCCAGGCAATGCCGTAGCTTGTGACAGCATA

27 千 column 7
row 3 page 1 行路难.txt

AGCTATACGGAGCATCGTGAGATTAGTCAACTAGCCTCACACCTCTATA
AGCCTCGAGTAGTATGAGTGGTGCTGATAGTACCAGAGCAGCTTCAGCT
ACATGTCCAGGCAATGCCGTAGCTTGTGACAGCATA

28 ， column 8 row
3 page 1 行路
难.txt

AGCTATACGGAGCATCGTGAGATTAGTCAACTAGCCTCACACCTCTATA
AGCCTCGAGTAGCACGGTCTCGATTGATAGTACCAGAGCCTAGCTCACT
ACATGTCCAGGCAATGCCGTAGCTTGTGACAGCATA

29 玉 column 9
row 3 page 1
行路难.txt

AGCTATACGGAGCATCGTGAGATTAGTCAACTAGCCTCACACCTCTATA
AGCCTCGAGTAGGCTATCAGGATATGATAGTACCAGAGCCTACACAGC
TACATGTCCAGGCAATGCCGTAGCTTGTGACAGCATA

30 盘 column 10
row 3 page 1 行路难.txt

AGCTATACGGAGCATCGTGAGATTAGTCAACTAGCCTCACACCTCTATA
AGCCTCGAGTAGATGTACTCCACGTGATAGTACCAGAGCTAGCCACTCT
ACATGTCCAGGCAATGCCGTAGCTTGTGACAGCATA

31 珍 column 11
  row 3 page 1 行路难.txt
AGCTATACGGAGCATCGTGAGATTAGTCAACTAGCCTCACACCTCTATA
AGCCTCGAGTAGTAGACTGAACGTTGATAGTACCAGAGCAGTGATGCC
TACATGTCCAGGCAATGCCGTAGCTTGTGACAGCATA 32 岩 column 12
  row 3 page 1 行路难.txt
AGCTATACGGAGCATCGTGAGATTAGTCAACTAGCCTCACACCTCTATA
AGCCTCGAGTAGGAGCTCTGCTGATGATAGTACCAGAGCCATCATGCCT
ACATGTCCAGGCAATGCCGTAGCTTGTGACAGCATA 33 立 column 13
  row 3 page 1 行路难.txt
AGCTATACGGAGCATCGTGAGATTAGTCAACTAGCCTCACACCTCTATA
AGCCTCGAGTAGTCACCACTTCTATGATAGTACCAGAGCTGCAACGTCT
ACATGTCCAGGCAATGCCGTAGCTTGTGACAGCATA 34 万 column 14
  row 3 page 1 行路难.txt
AGCTATACGGAGCATCGTGAGATTAGTCAACTAGCCTCACACCTCTATA
AGCCTCGAGTAGCGCACTCAATAGTGATAGTACCAGAGCACGCATCAC
TACATGTCCAGGCAATGCCGTAGCTTGTGACAGCATA 35 钱 column 15
  row 3 page 1 行路难.txt
AGCTATACGGAGCATCGTGAGATTAGTCAACTAGCCTCACACCTCTATA
AGCCTCGAGTAGTATCTACGACTGTGATAGTACCAGAGCGTGATGCTCT
ACATGTCCAGGCAATGCCGTAGCTTGTGACAGCATA 36 ○ column 16
  row 3 page 1
  行路难.txt
AGCTATACGGAGCATCGTGAGATTAGTCAACTAGCCTCACACCTCTATA
AGCCTCGAGTAGCACACATCTAGTTGATAGTACCAGAGCTGACCTAGCT
ACATGTCCAGGCAATGCCGTAGCTTGTGACAGCATA 37 \n column 17
  row 3 page 1
  行路难.txt
AGCTATACGGAGCATCGTGAGATTAGTCAACTAGCCTCACACCTCTATA
AGCCTCGAGTAGGTCAACGCTCATTGATAGTACCAGAGCTGTCACACCT
ACATGTCCAGGCAATGCCGTAGCTTGTGACAGCATA 38 停 column 1
  row 4 page 1
  行路难.txt
AGCTATACGGAGCATCGTGAGATTAGTCAACTAGCCTCCAGAGTACATA
AGCCTCGAGTAGTATGTATCGCTCTGATAGTACCAGAGCCAGAACGACT
ACATGTCCAGGCAATGCCGTAGCTTGTGACAGCATA 39 杯 column 2
  row 4 page 1
  行路难.txt
AGCTATACGGAGCATCGTGAGATTAGTCAACTAGCCTCCAGAGTACATA
AGCCTCGAGTAGTGACCTCGTGTCTGATAGTACCAGAGCAGCATCGACT
ACATGTCCAGGCAATGCCGTAGCTTGTGACAGCATA 40 投 column 3
  row 4 page 1
  行路难.txt
AGCTATACGGAGCATCGTGAGATTAGTCAACTAGCCTCCAGAGTACATA
AGCCTCGAGTAGCGTGGTACGTACTGATAGTACCAGAGCTGATGCTGCT
ACATGTCCAGGCAATGCCGTAGCTTGTGACAGCATA 41 箸 column 4
  row 4 page 1
  行路难.txt
AGCTATACGGAGCATCGTGAGATTAGTCAACTAGCCTCCAGAGTACATA
AGCCTCGAGTAGACTGCTCTCGTGTGATAGTACCAGAGCGATCCTGACT
ACATGTCCAGGCAATGCCGTAGCTTGTGACAGCATA 42 不 column 5
  row 4 page 1
  行路难.txt
AGCTATACGGAGCATCGTGAGATTAGTCAACTAGCCTCCAGAGTACATA
AGCCTCGAGTAGTCTCGCACAGCATGATAGTACCAGAGCACATCGCTCT
ACATGTCCAGGCAATGCCGTAGCTTGTGACAGCATA 43 能 column 6
  row 4 page
  1 行路难.txt
AGCTATACGGAGCATCGTGAGATTAGTCAACTAGCCTCCAGAGTACATA
AGCCTCGAGTAGGCGTACTAGAGTTGATAGTACCAGAGCGATGAGTGC
TACATGTCCAGGCAATGCCGTAGCTTGTGACAGCATA 44 食 column 7
  row 4 page
  1 行路难.txt
AGCTATACGGAGCATCGTGAGATTAGTCAACTAGCCTCCAGAGTACATA
AGCCTCGAGTAGTATGCAGTGACATGATAGTACCAGAGCAGCTTCAGCT
ACATGTCCAGGCAATGCCGTAGCTTGTGACAGCATA 45 , column 8 row
  4 page 1 行路
  难.txt
AGCTATACGGAGCATCGTGAGATTAGTCAACTAGCCTCCAGAGTACATA
AGCCTCGAGTAGCACGGTCTCGATTGATAGTACCAGAGCCTAGCTCACT
ACATGTCCAGGCAATGCCGTAGCTTGTGACAGCATA 46 拔 column 9
  row 4 page 1 行路难.txt
AGCTATACGGAGCATCGTGAGATTAGTCAACTAGCCTCCAGAGTACATA
AGCCTCGAGTAGAGTCACAGTGATTGATAGTACCAGAGCCTACACAGC
TACATGTCCAGGCAATGCCGTAGCTTGTGACAGCATA 47 剑 column 10
  row 4 page 1
  行路难.txt
AGCTATACGGAGCATCGTGAGATTAGTCAACTAGCCTCCAGAGTACATA
AGCCTCGAGTAGGATGACGATCTATGATAGTACCAGAGCTAGCCACTCT
ACATGTCCAGGCAATGCCGTAGCTTGTGACAGCATA 48 四 column 11
  row 4 page 1
  行路难.txt
AGCTATACGGAGCATCGTGAGATTAGTCAACTAGCCTCCAGAGTACATA
AGCCTCGAGTAGATGCGTAGCGTATGATAGTACCAGAGCAGTGATGCC
TACATGTCCAGGCAATGCCGTAGCTTGTGACAGCATA 49 顾 column 12
  row 4 page 1
  行路难.txt
AGCTATACGGAGCATCGTGAGATTAGTCAACTAGCCTCCAGAGTACATA
AGCCTCGAGTAGAGCTGCAGGATCTGATAGTACCAGAGCCATCATGCCT
ACATGTCCAGGCAATGCCGTAGCTTGTGACAGCATA 50 心 column 13
   row 4 page 1
   行路难.txt AGCTATACGGAGCATCGTGAGATTAGTCAACTAGCCTCCAGAGTACATA
AGCCTCGAGTAGTGAGTATACGACTGATAGTACCAGAGCTGCAACGTCT
ACATGTCCAGGCAATGCCGTAGCTTGTGACAGCATA 51 沦 column 14
   row 4 page 1 行路难.txt AGCTATACGGAGCATCGTGAGATTAGTCAACTAGCCTCCAGAGTACATA
AGCCTCGAGTAGGTGCATGCGTCTTGATAGTACCAGAGCACGCATCACT
ACATGTCCAGGCAATGCCGTAGCTTGTGACAGCATA 52 然 column 15
   row 4 page 1
   行路难.txt AGCTATACGGAGCATCGTGAGATTAGTCAACTAGCCTCCAGAGTACATA
AGCCTCGAGTAGCTCACACTACATTGATAGTACCAGAGCGTGATGCTCT
ACATGTCCAGGCAATGCCGTAGCTTGTGACAGCATA 53 ○ column 16
   row 4 page 1
   行路难.txt AGCTATACGGAGCATCGTGAGATTAGTCAACTAGCCTCCAGAGTACATA
AGCCTCGAGTAGCACACATCTAGTTGATAGTACCAGAGCTGACCTAGCT
ACATGTCCAGGCAATGCCGTAGCTTGTGACAGCATA 54 \n column 17
   row 4 page 1
   行路难.txt AGCTATACGGAGCATCGTGAGATTAGTCAACTAGCCTCCAGAGTACATA
AGCCTCGAGTAGGTCAACGCTCATTGATAGTACCAGAGCTGTCACACCT
ACATGTCCAGGCAATGCCGTAGCTTGTGACAGCATA 55 欲 column 1
   row 5 page 1 行路难.txt AGCTATACGGAGCATCGTGAGATTAGTCAACTAGCCTCACTGAGTCATA
AGCCTCGAGTAGTGTAGCGTGATATGATAGTACCAGAGCCAGAACGAC
TACATGTCCAGGCAATGCCGTAGCTTGTGACAGCATA 56 渡 column 2
   row 5 page 1 行路难.txt AGCTATACGGAGCATCGTGAGATTAGTCAACTAGCCTCACTGAGTCATA
AGCCTCGAGTAGCTCGAGTGTATATGATAGTACCAGAGCAGCATCGACT
ACATGTCCAGGCAATGCCGTAGCTTGTGACAGCATA 57 黄 column 3
   row 5 page 1 行路难.txt AGCTATACGGAGCATCGTGAGATTAGTCAACTAGCCTCACTGAGTCATA
AGCCTCGAGTAGTACTACTGCGTCTGATAGTACCAGAGCTGATGCTGCT
ACATGTCCAGGCAATGCCGTAGCTTGTGACAGCATA 58 河 column 4
   row 5 page 1 行路难.txt AGCTATACGGAGCATCGTGAGATTAGTCAACTAGCCTCACTGAGTCATA
AGCCTCGAGTAGTGTGGTGTGTACTGATAGTACCAGAGCGATCCTGACT
ACATGTCCAGGCAATGCCGTAGCTTGTGACAGCATA 59 冰 column 5
   row 5 page 1 行路难.txt AGCTATACGGAGCATCGTGAGATTAGTCAACTAGCCTCACTGAGTCATA
AGCCTCGAGTAGGCGACACTGATATGATAGTACCAGAGCACATCGCTCT
ACATGTCCAGGCAATGCCGTAGCTTGTGACAGCATA 60 塞 column 6
   row 5 page 1 行路难.txt AGCTATACGGAGCATCGTGAGATTAGTCAACTAGCCTCACTGAGTCATA
AGCCTCGAGTAGGCGAGATATAGATGATAGTACCAGAGCGATGAGTGC
TACATGTCCAGGCAATGCCGTAGCTTGTGACAGCATA 61 川 column 7
   row 5 page 1
   行路难.txt AGCTATACGGAGCATCGTGAGATTAGTCAACTAGCCTCACTGAGTCATA
AGCCTCGAGTAGCTGTGCTGCACATGATAGTACCAGAGCAGCTTCAGCT
ACATGTCCAGGCAATGCCGTAGCTTGTGACAGCATA 62 , column 8 row
   5 page 1 行路
   难.txt AGCTATACGGAGCATCGTGAGATTAGTCAACTAGCCTCACTGAGTCATA
AGCCTCGAGTAGCACGGTCTCGATTGATAGTACCAGAGCCTAGCTCACT
ACATGTCCAGGCAATGCCGTAGCTTGTGACAGCATA 63 将 column 9
   row 5 page 1 行路难.txt AGCTATACGGAGCATCGTGAGATTAGTCAACTAGCCTCACTGAGTCATA
AGCCTCGAGTAGTGACACTCACAGTGATAGTACCAGAGCCTACACAGC
TACATGTCCAGGCAATGCCGTAGCTTGTGACAGCATA 64 登 column 10
   row 5 page 1 行路难.txt AGCTATACGGAGCATCGTGAGATTAGTCAACTAGCCTCACTGAGTCATA
AGCCTCGAGTAGTATGTAGCTGCGTGATAGTACCAGAGCTAGCCACTCT
ACATGTCCAGGCAATGCCGTAGCTTGTGACAGCATA 65 太 column 11
   row 5 page 1 行路难.txt AGCTATACGGAGCATCGTGAGATTAGTCAACTAGCCTCACTGAGTCATA
AGCCTCGAGTAGCATCCATGCTGATGATAGTACCAGAGCAGTGATGCCT
ACATGTCCAGGCAATGCCGTAGCTTGTGACAGCATA 66 行 column 12
   row 5 page 1 行路难.txt AGCTATACGGAGCATCGTGAGATTAGTCAACTAGCCTCACTGAGTCATA
AGCCTCGAGTAGCGACGAGCCATATGATAGTACCAGAGCCATCATGCC
TACATGTCCAGGCAATGCCGTAGCTTGTGACAGCATA 67 雪 column 13
   row 5 page 1 行路难.txt AGCTATACGGAGCATCGTGAGATTAGTCAACTAGCCTCACTGAGTCATA
AGCCTCGAGTAGCGATGTGTTACTTGATAGTACCAGAGCTGCAACGTCT
ACATGTCCAGGCAATGCCGTAGCTTGTGACAGCATA 68 满 column 14
   row 5 page 1 行路难.txt AGCTATACGGAGCATCGTGAGATTAGTCAACTAGCCTCACTGAGTCATA
AGCCTCGAGTAGACATCTCGTCACTGATAGTACCAGAGCACGCATCACT
ACATGTCCAGGCAATGCCGTAGCTTGTGACAGCATA

| 69 | 山 column 15 row 5 page 1 行路难.txt | AGCTATACGGAGCATCGTGAGATTAGTCAACTAGCCTCACTGAGTCATA AGCCTCGAGTAGGTGCTACATAGTTGATAGTACCAGAGCGTGATGCTCT ACATGTCCAGGCAATGCCGTAGCTTGTGACAGCATA |
|---|---|---|
| 70 | ○ column 16 row 5 page 1 行路难.txt | AGCTATACGGAGCATCGTGAGATTAGTCAACTAGCCTCACTGAGTCATA AGCCTCGAGTAGCACACATCTAGTTGATAGTACCAGAGCTGACCTAGCT ACATGTCCAGGCAATGCCGTAGCTTGTGACAGCATA |
| 71 | \n column 17 row 5 page 1 行路难.txt | AGCTATACGGAGCATCGTGAGATTAGTCAACTAGCCTCACTGAGTCATA AGCCTCGAGTAGGTCAACGCTCATTGATAGTACCAGAGCTGTCACACCT ACATGTCCAGGCAATGCCGTAGCTTGTGACAGCATA |
| 72 | 闲 column 1 row 6 page 1 行路难.txt | AGCTATACGGAGCATCGTGAGATTAGTCAACTAGCCTCCTACGATGATA AGCCTCGAGTAGATAGGCATCGACTGATAGTACCAGAGCCAGAACGAC TACATGTCCAGGCAATGCCGTAGCTTGTGACAGCATA |
| 73 | 来 column 2 row 6 page 1 行路难.txt | AGCTATACGGAGCATCGTGAGATTAGTCAACTAGCCTCCTACGATGATA AGCCTCGAGTAGAGATCACGGCAGTGATAGTACCAGAGCAGCATCGAC TACATGTCCAGGCAATGCCGTAGCTTGTGACAGCATA |
| 74 | 垂 column 3 row 6 page 1 行路难.txt | AGCTATACGGAGCATCGTGAGATTAGTCAACTAGCCTCCTACGATGATA AGCCTCGAGTAGAGTCGAGAATCTTGATAGTACCAGAGCTGATGCTGCT ACATGTCCAGGCAATGCCGTAGCTTGTGACAGCATA |
| 75 | 钓 column 4 row 6 page 1 行路难.txt | AGCTATACGGAGCATCGTGAGATTAGTCAACTAGCCTCCTACGATGATA AGCCTCGAGTAGTAGCGAGCTCATTGATAGTACCAGAGCGATCCTGACT ACATGTCCAGGCAATGCCGTAGCTTGTGACAGCATA |
| 76 | 碧 column 5 row 6 page 1 行路难.txt | AGCTATACGGAGCATCGTGAGATTAGTCAACTAGCCTCCTACGATGATA AGCCTCGAGTAGGCGACAGTTACATGATAGTACCAGAGCACATCGCTCT ACATGTCCAGGCAATGCCGTAGCTTGTGACAGCATA |
| 77 | 溪 column 6 row 6 page 1 行路难.txt | AGCTATACGGAGCATCGTGAGATTAGTCAACTAGCCTCCTACGATGATA AGCCTCGAGTAGATCGATCTTCTCTGATAGTACCAGAGCGATGAGTGCT ACATGTCCAGGCAATGCCGTAGCTTGTGACAGCATA |
| 78 | 上 column 7 row 6 page 1 行路难.txt | AGCTATACGGAGCATCGTGAGATTAGTCAACTAGCCTCCTACGATGATA AGCCTCGAGTAGAGCACAGAACTGTGATAGTACCAGAGCAGCTTCAGC TACATGTCCAGGCAATGCCGTAGCTTGTGACAGCATA |
| 79 | , column 8 row 6 page 1 行路.txt 难.txt | AGCTATACGGAGCATCGTGAGATTAGTCAACTAGCCTCCTACGATGATA AGCCTCGAGTAGCACGGTCTCGATTGATAGTACCAGAGCCTAGCTCACT ACATGTCCAGGCAATGCCGTAGCTTGTGACAGCATA |
| 80 | 忽 column 9 row 6 page 1 行路难.txt | AGCTATACGGAGCATCGTGAGATTAGTCAACTAGCCTCCTACGATGATA AGCCTCGAGTAGCAGCTGACTCACTGATAGTACCAGAGCCTACACAGCT ACATGTCCAGGCAATGCCGTAGCTTGTGACAGCATA |
| 81 | 复 column 10 row 6 page 1 行路难.txt | AGCTATACGGAGCATCGTGAGATTAGTCAACTAGCCTCCTACGATGATA AGCCTCGAGTAGCAGCCTGACATGTGATAGTACCAGAGCTAGCCACTCT ACATGTCCAGGCAATGCCGTAGCTTGTGACAGCATA |
| 82 | 乘 column 11 row 6 page 1 行路难.txt | AGCTATACGGAGCATCGTGAGATTAGTCAACTAGCCTCCTACGATGATA AGCCTCGAGTAGACTCTGCATCATTGATAGTACCAGAGCAGTGATGCCT ACATGTCCAGGCAATGCCGTAGCTTGTGACAGCATA |
| 83 | 舟 column 12 row 6 page 1 行路难.txt | AGCTATACGGAGCATCGTGAGATTAGTCAACTAGCCTCCTACGATGATA AGCCTCGAGTAGTCATAGCGATCTTGATAGTACCAGAGCCATCATGCCT ACATGTCCAGGCAATGCCGTAGCTTGTGACAGCATA |
| 84 | 梦 column 13 row 6 page 1 行路难.txt | AGCTATACGGAGCATCGTGAGATTAGTCAACTAGCCTCCTACGATGATA AGCCTCGAGTAGTATCGCTGTGTGTGATAGTACCAGAGCTGCAACGTCT ACATGTCCAGGCAATGCCGTAGCTTGTGACAGCATA |
| 85 | 日 column 14 row 6 page 1 行路难.txt | AGCTATACGGAGCATCGTGAGATTAGTCAACTAGCCTCCTACGATGATA AGCCTCGAGTAGGTGACGCGTGTATGATAGTACCAGAGCACGCATCAC TACATGTCCAGGCAATGCCGTAGCTTGTGACAGCATA |
| 86 | 边 column 15 row 6 page 1 行路难.txt | AGCTATACGGAGCATCGTGAGATTAGTCAACTAGCCTCCTACGATGATA AGCCTCGAGTAGCGCACTGCATGATGATAGTACCAGAGCGTGATGCTCT ACATGTCCAGGCAATGCCGTAGCTTGTGACAGCATA |

-continued

| | |
|---|---|
| 87○<br>  column 16<br>  row 6 page 1 行路难.txt | AGCTATACGGAGCATCGTGAGATTAGTCAACTAGCCTCCTACGATGATA<br>AGCCTCGAGTAGCACACATCTAGTTGATAGTACCAGAGCTGACCTAGCT<br>ACATGTCCAGGCAATGCCGTAGCTTGTGACAGCATA |
| 88\n column 17<br>  row 6 page 1 行路难.txt | AGCTATACGGAGCATCGTGAGATTAGTCAACTAGCCTCCTACGATGATA<br>AGCCTCGAGTAGGTCAACGCTCATTGATAGTACCAGAGCTGTCACACCT<br>ACATGTCCAGGCAATGCCGTAGCTTGTGACAGCATA |
| 89 行 column 1<br>  row 7 page 1<br>  行路难.txt | AGCTATACGGAGCATCGTGAGATTAGTCAACTAGCCTCGCAGATGTATA<br>AGCCTCGAGTAGCGACGAGCCATATGATAGTACCAGAGCCAGAACGAC<br>TACATGTCCAGGCAATGCCGTAGCTTGTGACAGCATA |
| 90 路 column 2<br>  row 7 page 1 行路难.txt | AGCTATACGGAGCATCGTGAGATTAGTCAACTAGCCTCGCAGATGTATA<br>AGCCTCGAGTAGCTCAGATGGCATTGATAGTACCAGAGCAGCATCGAC<br>TACATGTCCAGGCAATGCCGTAGCTTGTGACAGCATA |
| 91 难 column 3<br>  row 7 page 1 行路难.txt | AGCTATACGGAGCATCGTGAGATTAGTCAACTAGCCTCGCAGATGTATA<br>AGCCTCGAGTAGACTCTAGTGTGATGATAGTACCAGAGCTGATGCTGCT<br>ACATGTCCAGGCAATGCCGTAGCTTGTGACAGCATA |
| 92 ! column 4<br>  row 7 page 1<br>  行路难.txt | AGCTATACGGAGCATCGTGAGATTAGTCAACTAGCCTCGCAGATGTATA<br>AGCCTCGAGTAGATATGTGCGTGTTGATAGTACCAGAGCGATCCTGACT<br>ACATGTCCAGGCAATGCCGTAGCTTGTGACAGCATA |
| 93 行 column 5<br>  row 7 page 1<br>  行路难.txt | AGCTATACGGAGCATCGTGAGATTAGTCAACTAGCCTCGCAGATGTATA<br>AGCCTCGAGTAGCGACGAGCCATATGATAGTACCAGAGCACATCGCTC<br>TACATGTCCAGGCAATGCCGTAGCTTGTGACAGCATA |
| 94 路 column 6<br>  row 7 page 1<br>  行路难.txt | AGCTATACGGAGCATCGTGAGATTAGTCAACTAGCCTCGCAGATGTATA<br>AGCCTCGAGTAGCTCAGATGGCATTGATAGTACCAGAGCGATGAGTGC<br>TACATGTCCAGGCAATGCCGTAGCTTGTGACAGCATA |
| 95 难 column 7<br>  row 7 page<br>  1 行路难.txt | AGCTATACGGAGCATCGTGAGATTAGTCAACTAGCCTCGCAGATGTATA<br>AGCCTCGAGTAGACTCTAGTGTGATGATAGTACCAGAGCAGCTTCAGCT<br>ACATGTCCAGGCAATGCCGTAGCTTGTGACAGCATA |
| 96 行路 column 8<br>  Row 7 page 1<br>  难.txt | AGCTATACGGAGCATCGTGAGATTAGTCAACTAGCCTCGCAGATGTATA<br>AGCCTCGAGTAGATATGTGCGTGTTGATAGTACCAGAGCCTAGCTCACT<br>ACATGTCCAGGCAATGCCGTAGCTTGTGACAGCATA |
| 97 多 column 9<br>  row 7 page 1<br>  行路难.txt | AGCTATACGGAGCATCGTGAGATTAGTCAACTAGCCTCGCAGATGTATA<br>AGCCTCGAGTAGCTCGCTGTACTATGATAGTACCAGAGCCTACACAGCT<br>ACATGTCCAGGCAATGCCGTAGCTTGTGACAGCATA |
| 98 歧 column 10<br>  row 7 page 1<br>  行路难.txt | AGCTATACGGAGCATCGTGAGATTAGTCAACTAGCCTCGCAGATGTATA<br>AGCCTCGAGTAGACAGGCTGAGCTTGATAGTACCAGAGCTAGCCACTCT<br>ACATGTCCAGGCAATGCCGTAGCTTGTGACAGCATA |
| 99 路 column 11<br>  row 7 page<br>  1 行路难.txt | AGCTATACGGAGCATCGTGAGATTAGTCAACTAGCCTCGCAGATGTATA<br>AGCCTCGAGTAGCTCAGATGGCATTGATAGTACCAGAGCAGTGATGCCT<br>ACATGTCCAGGCAATGCCGTAGCTTGTGACAGCATA |
| 100 , column 12<br>  row 7 page 1<br>  行路难.txt | AGCTATACGGAGCATCGTGAGATTAGTCAACTAGCCTCGCAGATGTATA<br>AGCCTCGAGTAGCACGGTCTCGATTGATAGTACCAGAGCCATCATGCCT<br>ACATGTCCAGGCAATGCCGTAGCTTGTGACAGCATA |
| 101 今 column 13<br>  row 7 page 1 行路难.txt | AGCTATACGGAGCATCGTGAGATTAGTCAACTAGCCTCGCAGATGTATA<br>AGCCTCGAGTAGGCATGTAGGCTCTGATAGTACCAGAGCTGCAACGTCT<br>ACATGTCCAGGCAATGCCGTAGCTTGTGACAGCATA |
| 102 安 column 14<br>  row 7 page 1 行路难.txt | AGCTATACGGAGCATCGTGAGATTAGTCAACTAGCCTCGCAGATGTATA<br>AGCCTCGAGTAGGTCTGAGATGATTGATAGTACCAGAGCACGCATCACT<br>ACATGTCCAGGCAATGCCGTAGCTTGTGACAGCATA |
| 103 在 column 15<br>  row 7 page 1 行路难.txt | AGCTATACGGAGCATCGTGAGATTAGTCAACTAGCCTCGCAGATGTATA<br>AGCCTCGAGTAGACATGACTGCGTTGATAGTACCAGAGCGTGATGCTCT<br>ACATGTCCAGGCAATGCCGTAGCTTGTGACAGCATA |
| 104 ? column 16<br>  row 7 page 1 行路难.txt | AGCTATACGGAGCATCGTGAGATTAGTCAACTAGCCTCGCAGATGTATA<br>AGCCTCGAGTAGATCACATGACTCTGATAGTACCAGAGCTGACCTAGCT<br>ACATGTCCAGGCAATGCCGTAGCTTGTGACAGCATA |
| 105 \n column 17<br>  row 7 page 1 行路难.txt | AGCTATACGGAGCATCGTGAGATTAGTCAACTAGCCTCGCAGATGTATA<br>AGCCTCGAGTAGGTCAACGCTCATTGATAGTACCAGAGCTGTCACACCT<br>ACATGTCCAGGCAATGCCGTAGCTTGTGACAGCATA |

-continued

```
106 长 column 1        AGCTATACGGAGCATCGTGAGATTAGTCAACTAGCCTCGTCATCGTATA
    row 8 page         AGCCTCGAGTAGGCGTAGCTGTACTGATAGTACCAGAGCCAGAACGAC
    1 行路难.txt        TACATGTCCAGGCAATGCCGTAGCTTGTGACAGCATA 107 风 column 2        AGCTATACGGAGCATCGTGAGATTAGTCAACTAGCCTCGTCATCGTATA
    row 8 page 1 行路难.txt  AGCCTCGAGTAGGCAGGACACTGTTGATAGTACCAGAGCAGCATCGAC
                       TACATGTCCAGGCAATGCCGTAGCTTGTGACAGCATA 108 破 column 3        AGCTATACGGAGCATCGTGAGATTAGTCAACTAGCCTCGTCATCGTATA
    row 8 page 1 行路难.txt  AGCCTCGAGTAGGACGGTCAAGTGTGATAGTACCAGAGCTGATGCTGC
                       TACATGTCCAGGCAATGCCGTAGCTTGTGACAGCATA 109 浪 column 4        AGCTATACGGAGCATCGTGAGATTAGTCAACTAGCCTCGTCATCGTATA
    row 8 page 1 行路难.txt  AGCCTCGAGTAGTGCGCATGACAGTGATAGTACCAGAGCGATCCTGAC
                       TACATGTCCAGGCAATGCCGTAGCTTGTGACAGCATA 110 会 column 5        AGCTATACGGAGCATCGTGAGATTAGTCAACTAGCCTCGTCATCGTATA
    row 8 page 1 行路难.txt  AGCCTCGAGTAGACTAATACGTCGTGATAGTACCAGAGCACATCGCTCT
                       ACATGTCCAGGCAATGCCGTAGCTTGTGACAGCATA 111 有 column 6        AGCTATACGGAGCATCGTGAGATTAGTCAACTAGCCTCGTCATCGTATA
    row 8 page 1 行路难.txt  AGCCTCGAGTAGCTACCGACTCTGTGATAGTACCAGAGCGATGAGTGCT
                       ACATGTCCAGGCAATGCCGTAGCTTGTGACAGCATA 112 column 7          AGCTATACGGAGCATCGTGAGATTAGTCAACTAGCCTCGTCATCGTATA
    row 8 page 1       AGCCTCGAGTAGTCTCACAGTAGCTGATAGTACCAGAGCAGCTTCAGCT
    时行路难.txt        ACATGTCCAGGCAATGCCGTAGCTTGTGACAGCATA 113, column 8 row     AGCTATACGGAGCATCGTGAGATTAGTCAACTAGCCTCGTCATCGTATA
    8 page 1 行路       AGCCTCGAGTAGCACGGTCTCGATTGATAGTACCAGAGCCTAGCTCACT
    难.txt             ACATGTCCAGGCAATGCCGTAGCTTGTGACAGCATA 114 直 column 9        AGCTATACGGAGCATCGTGAGATTAGTCAACTAGCCTCGTCATCGTATA
    row 8 page 1       AGCCTCGAGTAGTCACCACTTCTATGATAGTACCAGAGCCTACACAGCT
    行路难.txt          ACATGTCCAGGCAATGCCGTAGCTTGTGACAGCATA 115 挂 column 10       AGCTATACGGAGCATCGTGAGATTAGTCAACTAGCCTCGTCATCGTATA
    row 8 page 1 行路难.txt  AGCCTCGAGTAGAGCTCACAGCGTTGATAGTACCAGAGCTAGCCACTCT
                       ACATGTCCAGGCAATGCCGTAGCTTGTGACAGCATA 116 云 column 11       AGCTATACGGAGCATCGTGAGATTAGTCAACTAGCCTCGTCATCGTATA
    row 8 page 1 行路难.txt  AGCCTCGAGTAGCGAGGATCACACTGATAGTACCAGAGCAGTGATGCC
                       TACATGTCCAGGCAATGCCGTAGCTTGTGACAGCATA 117 帆 column 12       AGCTATACGGAGCATCGTGAGATTAGTCAACTAGCCTCGTCATCGTATA
    row 8 page 1 行路难.txt  AGCCTCGAGTAGAGCTTGACGTATTGATAGTACCAGAGCCATCATGCCT
                       ACATGTCCAGGCAATGCCGTAGCTTGTGACAGCATA 118 济 column 13       AGCTATACGGAGCATCGTGAGATTAGTCAACTAGCCTCGTCATCGTATA
    row 8 page 1 行路难.txt  AGCCTCGAGTAGTGAGTCAGACATTGATAGTACCAGAGCTGCAACGTCT
                       ACATGTCCAGGCAATGCCGTAGCTTGTGACAGCATA 119 沧 column 14       AGCTATACGGAGCATCGTGAGATTAGTCAACTAGCCTCGTCATCGTATA
    row 8 page 1 行路难.txt  AGCCTCGAGTAGTAGTACTGTCGCTGATAGTACCAGAGCACGCATCACT
                       ACATGTCCAGGCAATGCCGTAGCTTGTGACAGCATA 120 海 column 15       AGCTATACGGAGCATCGTGAGATTAGTCAACTAGCCTCGTCATCGTATA
    row 8 page 1 行路难.txt  AGCCTCGAGTAGTGTGCTATCACTTGATAGTACCAGAGCGTGATGCTCT
                       ACATGTCCAGGCAATGCCGTAGCTTGTGACAGCATA 121 ○                 AGCTATACGGAGCATCGTGAGATTAGTCAACTAGCCTCGTCATCGTATA
    column 16          AGCCTCGAGTAGCACACATCTAGTTGATAGTACCAGAGCTGACCTAGCT
    row 8 page 1 行路难.txt  ACATGTCCAGGCAATGCCGTAGCTTGTGACAGCATA
```

Although the disclosure has been described with reference to the exemplary embodiments, it should be understood that the disclosure is not limited to the disclosed exemplary embodiments. Without departing from the scope or spirit of the disclosure, various adjustments or changes can be made to the exemplary embodiments of the present specification. The scope of the claims should be based on the broadest interpretation to cover all modifications and equivalent structures and functions.

What is claimed:

1. A method for DNA movable type storage mainly comprising:

(1) constructing a physical movable type library of payloads and a physical movable type library of indexes based on DNA movable type codebook, wherein the physical movable type library of payloads consists of a variety of DNA oligonucleotides, each corresponding to a DNA payload movable type element and stored separately, wherein the physical movable type library of indexes consists of a variety of DNA oligonucleotides, each corresponding to a DNA index movable type element and stored separately, wherein each of the DNA oligonucleotides comprises two linkers, (2) dividing the binary data of the target storage file into a plurality of data units, for each data unit, based on the DNA movable type codebook, transcoding the data unit into a DNA payload movable type element and assigning at least one corresponding DNA index movable type element based on the DNA movable type encoding principle from DNA movable type codebook, and mapping each the DNA payload movable type element and DNA index movable type element to its corresponding DNA oligonucleotide from the two abovementioned libraries based on DNA movable type encoding principle from DNA movable type codebook, wherein, a DNA payload movable type element and at least one corresponding DNA index movable type element, linked together via the linkers, collectively define a DNA movable type unit; wherein the linkers are configured to realize the linking and assembling of the DNA payload movable type element and the DNA index movable type element into a DNA movable type unit;

wherein, each the DNA movable type unit comprises, in a physical form, one DNA payload movable type sequence, a plurality of DNA index movable type sequences, and a plurality of linker sequences;

wherein, the DNA movable type unit comprises in a linked form: a first DNA index movable type sequence, a first linker sequence, a DNA payload movable type sequence, a second linker, and a second index movable type sequence; wherein the first and second linkers are different and the first and second index movable type sequences are different, (3) linking, via the linkers, the DNA oligonucleotides corresponding to the DNA payload movable type elements with the DNA oligonucleotides corresponding to the DNA index movable type elements mapped in step (2), to generate physical DNA movable type units, and then combining all generated DNA movable type units to form a DNA data storage library, which covers all data information of the target file, and (4) sequencing all oligonucleotides in the storage library generated in step (3), and decoding the sequencing results into the binary data of the target storage file based on DNA movable type decoding principle from DNA movable type codebook.

2. The method for DNA movable type storage according to claim 1, wherein binary data of the target storage file are selected from at least one of text, image, audio and video.

3. The method for DNA movable type storage according to claim 1, wherein the DNA payload movable type elements are selected from at least one of a character, a pixel, an audio amplitude and a video frame; and the DNA index movable type elements comprise location and attribute information of a DNA payload movable type element.

4. The method for DNA movable type storage according to claim 3, wherein the location information of a DNA payload movable type elements comprises information of page number, row and column.

5. The method for DNA movable type storage according to claim 3, wherein the attribute information of a DNA payload movable type element comprises file type, file name, file size, and creation time.

6. The method for DNA movable type storage according to claim 1, wherein the linkers are comprised among the oligonucleotides of DNA payload movable type elements and the oligonucleotides of DNA index movable type elements in a DNA movable type unit.

7. The method for DNA movable type storage according to claim 6, wherein the linker sequences are overlapping sequences or enzymatically cleavable linker sequences.

8. A system for DNA movable type storage comprising:
a. a library of DNA oligonucleotides corresponding to all DNA payload movable type elements and a library of DNA oligonucleotides corresponding to all DNA index movable type elements;
b. an encoding module/software provided for splitting binary data of the target storage file into a plurality of data units; for each unit, based on the DNA movable type codebook, transcoding the data unit into a DNA payload movable type element and assigning at least one corresponding DNA index movable type element based on the DNA movable type encoding principle from DNA movable type codebook, and
mapping each the DNA payload movable type element and the DNA index movable type element to its corresponding DNA oligonucleotide from the two abovementioned libraries based on DNA movable type encoding principle from DNA movable type codebook;
linking the mapped DNA oligonucleotides to form DNA movable type units, wherein a DNA payload movable type element and at least one corresponding DNA index movable type element, linked together via linkers, collectively define a DNA movable type unit; wherein the linkers are configured to realize the linking and assembling of the DNA payload movable type element and the DNA index movable type element into a DNA movable type unit;
wherein each the DNA movable type unit comprises, in a physical form, one DNA payload movable type sequence, and a plurality of linker sequences, a plurality of index movable type sequences,
wherein the DNA movable type unit comprises in a linked form, a first DNA index movable type sequence, a first linker sequence, the DNA payload movable type sequence, a second linker sequence, and a second index movable type sequence, wherein the first and second linkers are different and the first and second index movable type sequences are different, and
c. a decoding module/software provided for decoding the sequencing data from the oligonucleotides in a library for a DNA movable type storage file into corresponding binary data of target storage file, according to DNA movable type encoding principle from DNA movable type codebook using a corresponding decoding software.

9. The system for DNA movable type storage according to claim 8, wherein the system further comprises a system for DNA linker design and a system for DNA sequencing.

* * * * *

SEQUENCE LISTING

<160> NUMBER OF SEQ ID NOS: 156

<210> SEQ ID NO 1
<211> LENGTH: 42
<212> TYPE: DNA
<213> ORGANISM: Artificial Sequence
<220> FEATURE:
<223> OTHER INFORMATION: Synthesized

<400> SEQUENCE: 1
ataagcctcg agtaggcgta gctgtactga tagtaccaga gc                          42

<210> SEQ ID NO 2
<211> LENGTH: 42
<212> TYPE: DNA
<213> ORGANISM: Artificial Sequence
<220> FEATURE:
<223> OTHER INFORMATION: Synthesized

<400> SEQUENCE: 2
ataagcctcg agtaggcagg acactgttga tagtaccaga gc                          42

<210> SEQ ID NO 3
<211> LENGTH: 42
<212> TYPE: DNA
<213> ORGANISM: Artificial Sequence
<220> FEATURE:
<223> OTHER INFORMATION: Synthesized

<400> SEQUENCE: 3
ataagcctcg agtaggacgg tcaagtgtga tagtaccaga gc                          42

<210> SEQ ID NO 4
<211> LENGTH: 42
<212> TYPE: DNA
<213> ORGANISM: Artificial Sequence
<220> FEATURE:
<223> OTHER INFORMATION: Synthesized

<400> SEQUENCE: 4
ataagcctcg agtagtgcgc atgacagtga tagtaccaga gc                          42

<210> SEQ ID NO 5
<211> LENGTH: 42
<212> TYPE: DNA
<213> ORGANISM: Artificial Sequence
<220> FEATURE:
<223> OTHER INFORMATION: Synthesized

<400> SEQUENCE: 5
ataagcctcg agtagactaa tacgtcgtga tagtaccaga gc                          42

<210> SEQ ID NO 6
<211> LENGTH: 42
<212> TYPE: DNA
<213> ORGANISM: Artificial Sequence
<220> FEATURE:
<223> OTHER INFORMATION: Synthesized

<400> SEQUENCE: 6
ataagcctcg agtagctacc gactctgtga tagtaccaga gc                          42

<210> SEQ ID NO 7
<211> LENGTH: 42
<212> TYPE: DNA
<213> ORGANISM: Artificial Sequence -continued

```
<220> FEATURE:
<223> OTHER INFORMATION: Synthesized

<400> SEQUENCE: 7
ataagcctcg agtagtctca cagtagctga tagtaccaga gc                        42

<210> SEQ ID NO 8
<211> LENGTH: 42
<212> TYPE: DNA
<213> ORGANISM: Artificial Sequence
<220> FEATURE:
<223> OTHER INFORMATION: Synthesized

<400> SEQUENCE: 8
ataagcctcg agtagcacgg tctcgattga tagtaccaga gc                        42

<210> SEQ ID NO 9
<211> LENGTH: 42
<212> TYPE: DNA
<213> ORGANISM: Artificial Sequence
<220> FEATURE:
<223> OTHER INFORMATION: Synthesized

<400> SEQUENCE: 9
ataagcctcg agtagtcacc acttctatga tagtaccaga gc                        42

<210> SEQ ID NO 10
<211> LENGTH: 42
<212> TYPE: DNA
<213> ORGANISM: Artificial Sequence
<220> FEATURE:
<223> OTHER INFORMATION: Synthesized

<400> SEQUENCE: 10
ataagcctcg agtagagctc acagcgttga tagtaccaga gc                        42

<210> SEQ ID NO 11
<211> LENGTH: 42
<212> TYPE: DNA
<213> ORGANISM: Artificial Sequence
<220> FEATURE:
<223> OTHER INFORMATION: Synthesized

<400> SEQUENCE: 11
ataagcctcg agtagcgagg atcacactga tagtaccaga gc                        42

<210> SEQ ID NO 12
<211> LENGTH: 42
<212> TYPE: DNA
<213> ORGANISM: Artificial Sequence
<220> FEATURE:
<223> OTHER INFORMATION: Synthesized

<400> SEQUENCE: 12
ataagcctcg agtagagctt gacgtattga tagtaccaga gc                        42

<210> SEQ ID NO 13
<211> LENGTH: 42
<212> TYPE: DNA
<213> ORGANISM: Artificial Sequence
<220> FEATURE:
<223> OTHER INFORMATION: Synthesized

<400> SEQUENCE: 13
ataagcctcg agtagtgagt cagacattga tagtaccaga gc                        42
```

-continued

```
<210> SEQ ID NO 14
<211> LENGTH: 42
<212> TYPE: DNA
<213> ORGANISM: Artificial Sequence
<220> FEATURE:
<223> OTHER INFORMATION: Synthesized

<400> SEQUENCE: 14
ataagcctcg agtagtagta ctgtcgctga tagtaccaga gc                            42

<210> SEQ ID NO 15
<211> LENGTH: 42
<212> TYPE: DNA
<213> ORGANISM: Artificial Sequence
<220> FEATURE:
<223> OTHER INFORMATION: Synthesized

<400> SEQUENCE: 15
ataagcctcg agtagtgtgc tatcacttga tagtaccaga gc                            42

<210> SEQ ID NO 16
<211> LENGTH: 42
<212> TYPE: DNA
<213> ORGANISM: Artificial Sequence
<220> FEATURE:
<223> OTHER INFORMATION: Synthesized

<400> SEQUENCE: 16
ataagcctcg agtagcacac atctagttga tagtaccaga gc                            42

<210> SEQ ID NO 17
<211> LENGTH: 38
<212> TYPE: DNA
<213> ORGANISM: Artificial Sequence
<220> FEATURE:
<223> OTHER INFORMATION: Synthesized

<400> SEQUENCE: 17
agctatacgg agcatcgtga gattagtcaa ctagcctc                                 38

<210> SEQ ID NO 18
<211> LENGTH: 38
<212> TYPE: DNA
<213> ORGANISM: Artificial Sequence
<220> FEATURE:
<223> OTHER INFORMATION: Synthesized

<400> SEQUENCE: 18
ctacatgtcc aggcaatgcc gtagcttgtg acagcata                                 38

<210> SEQ ID NO 19
<211> LENGTH: 38
<212> TYPE: DNA
<213> ORGANISM: Artificial Sequence
<220> FEATURE:
<223> OTHER INFORMATION: Synthesized

<400> SEQUENCE: 19
tagtcaacta gcctcgtcat cgtataagcc tcgagtag                                 38

<210> SEQ ID NO 20
<211> LENGTH: 38
<212> TYPE: DNA
<213> ORGANISM: Artificial Sequence
<220> FEATURE:
<223> OTHER INFORMATION: Synthesized
```

-continued

```
<400> SEQUENCE: 20
tgatagtacc agagccagaa cgactacatg tccaggca                    38

<210> SEQ ID NO 21
<211> LENGTH: 38
<212> TYPE: DNA
<213> ORGANISM: Artificial Sequence
<220> FEATURE:
<223> OTHER INFORMATION: Synthesized

<400> SEQUENCE: 21
tgatagtacc agagcagcat cgactacatg tccaggca                    38

<210> SEQ ID NO 22
<211> LENGTH: 38
<212> TYPE: DNA
<213> ORGANISM: Artificial Sequence
<220> FEATURE:
<223> OTHER INFORMATION: Synthesized

<400> SEQUENCE: 22
tgatagtacc agagctgatg ctgctacatg tccaggca                    38

<210> SEQ ID NO 23
<211> LENGTH: 38
<212> TYPE: DNA
<213> ORGANISM: Artificial Sequence
<220> FEATURE:
<223> OTHER INFORMATION: Synthesized

<400> SEQUENCE: 23
tgatagtacc agagcgatcc tgactacatg tccaggca                    38

<210> SEQ ID NO 24
<211> LENGTH: 38
<212> TYPE: DNA
<213> ORGANISM: Artificial Sequence
<220> FEATURE:
<223> OTHER INFORMATION: Synthesized

<400> SEQUENCE: 24
tgatagtacc agagcacatc gctctacatg tccaggca                    38

<210> SEQ ID NO 25
<211> LENGTH: 38
<212> TYPE: DNA
<213> ORGANISM: Artificial Sequence
<220> FEATURE:
<223> OTHER INFORMATION: Synthesized

<400> SEQUENCE: 25
tgatagtacc agagcgatga gtgctacatg tccaggca                    38

<210> SEQ ID NO 26
<211> LENGTH: 38
<212> TYPE: DNA
<213> ORGANISM: Artificial Sequence
<220> FEATURE:
<223> OTHER INFORMATION: Synthesized

<400> SEQUENCE: 26
tgatagtacc agagcagctt cagctacatg tccaggca                    38

<210> SEQ ID NO 27
```

-continued

```
<211> LENGTH: 38
<212> TYPE: DNA
<213> ORGANISM: Artificial Sequence
<220> FEATURE:
<223> OTHER INFORMATION: Synthesized

<400> SEQUENCE: 27
tgatagtacc agagcctagc tcactacatg tccaggca                              38

<210> SEQ ID NO 28
<211> LENGTH: 38
<212> TYPE: DNA
<213> ORGANISM: Artificial Sequence
<220> FEATURE:
<223> OTHER INFORMATION: Synthesized

<400> SEQUENCE: 28
tgatagtacc agagcctaca cagctacatg tccaggca                              38

<210> SEQ ID NO 29
<211> LENGTH: 38
<212> TYPE: DNA
<213> ORGANISM: Artificial Sequence
<220> FEATURE:
<223> OTHER INFORMATION: Synthesized

<400> SEQUENCE: 29
tgatagtacc agagctagcc actctacatg tccaggca                              38

<210> SEQ ID NO 30
<211> LENGTH: 38
<212> TYPE: DNA
<213> ORGANISM: Artificial Sequence
<220> FEATURE:
<223> OTHER INFORMATION: Synthesized

<400> SEQUENCE: 30
tgatagtacc agagcagtga tgcctacatg tccaggca                              38

<210> SEQ ID NO 31
<211> LENGTH: 38
<212> TYPE: DNA
<213> ORGANISM: Artificial Sequence
<220> FEATURE:
<223> OTHER INFORMATION: Synthesized

<400> SEQUENCE: 31
tgatagtacc agagccatca tgcctacatg tccaggca                              38

<210> SEQ ID NO 32
<211> LENGTH: 38
<212> TYPE: DNA
<213> ORGANISM: Artificial Sequence
<220> FEATURE:
<223> OTHER INFORMATION: Synthesized

<400> SEQUENCE: 32
tgatagtacc agagctgcaa cgtctacatg tccaggca                              38

<210> SEQ ID NO 33
<211> LENGTH: 38
<212> TYPE: DNA
<213> ORGANISM: Artificial Sequence
<220> FEATURE:
<223> OTHER INFORMATION: Synthesized

<400> SEQUENCE: 33
```

-continued tgatagtacc agagcacgca tcactacatg tccaggca                                    38

<210> SEQ ID NO 34
<211> LENGTH: 38
<212> TYPE: DNA
<213> ORGANISM: Artificial Sequence
<220> FEATURE:
<223> OTHER INFORMATION: Synthesized

<400> SEQUENCE: 34
tgatagtacc agagcgtgat gctctacatg tccaggca                                    38

<210> SEQ ID NO 35
<211> LENGTH: 38
<212> TYPE: DNA
<213> ORGANISM: Artificial Sequence
<220> FEATURE:
<223> OTHER INFORMATION: Synthesized

<400> SEQUENCE: 35
tgatagtacc agagctgacc tagctacatg tccaggca                                    38

<210> SEQ ID NO 36
<211> LENGTH: 134
<212> TYPE: DNA
<213> ORGANISM: Artificial Sequence
<220> FEATURE:
<223> OTHER INFORMATION: Synthesized

<400> SEQUENCE: 36
agctatacgg agcatcgtga gattagtcaa ctagcctcac acatgcataa gcctcgagta      60
gcgacgagcc atatgatagt accagagcca gaacgactac atgtccaggc aatgccgtag     120
cttgtgacag cata                                                        134

<210> SEQ ID NO 37
<211> LENGTH: 134
<212> TYPE: DNA
<213> ORGANISM: Artificial Sequence
<220> FEATURE:
<223> OTHER INFORMATION: Synthesized

<400> SEQUENCE: 37
agctatacgg agcatcgtga gattagtcaa ctagcctcac acatgcataa gcctcgagta      60
gctcagatgg cattgatagt accagagcag catcgactac atgtccaggc aatgccgtag     120
cttgtgacag cata                                                        134

<210> SEQ ID NO 38
<211> LENGTH: 134
<212> TYPE: DNA
<213> ORGANISM: Artificial Sequence
<220> FEATURE:
<223> OTHER INFORMATION: Synthesized

<400> SEQUENCE: 38
agctatacgg agcatcgtga gattagtcaa ctagcctcac acatgcataa gcctcgagta      60
gactctagtg tgatgatagt accagagctg atgctgctac atgtccaggc aatgccgtag     120
cttgtgacag cata                                                        134

<210> SEQ ID NO 39
<211> LENGTH: 134
<212> TYPE: DNA

-continued

```
<213> ORGANISM: Artificial Sequence
<220> FEATURE:
<223> OTHER INFORMATION: Synthesized

<400> SEQUENCE: 39
agctatacgg agcatcgtga gattagtcaa ctagcctcac acatgcataa gcctcgagta        60
ggatggcgtg agatgatagt accagagcga tcctgactac atgtccaggc aatgccgtag       120
cttgtgacag cata                                                         134

<210> SEQ ID NO 40
<211> LENGTH: 134
<212> TYPE: DNA
<213> ORGANISM: Artificial Sequence
<220> FEATURE:
<223> OTHER INFORMATION: Synthesized

<400> SEQUENCE: 40
agctatacgg agcatcgtga gattagtcaa ctagcctcac acatgcataa gcctcgagta        60
gacagcgacc tgatgatagt accagagcac atcgctctac atgtccaggc aatgccgtag       120
cttgtgacag cata                                                         134

<210> SEQ ID NO 41
<211> LENGTH: 134
<212> TYPE: DNA
<213> ORGANISM: Artificial Sequence
<220> FEATURE:
<223> OTHER INFORMATION: Synthesized

<400> SEQUENCE: 41
agctatacgg agcatcgtga gattagtcaa ctagcctcac acatgcataa gcctcgagta        60
ggtatcacgt gcgtgatagt accagagcga tgagtgctac atgtccaggc aatgccgtag       120
cttgtgacag cata                                                         134

<210> SEQ ID NO 42
<211> LENGTH: 134
<212> TYPE: DNA
<213> ORGANISM: Artificial Sequence
<220> FEATURE:
<223> OTHER INFORMATION: Synthesized

<400> SEQUENCE: 42
agctatacgg agcatcgtga gattagtcaa ctagcctcac acatgcataa gcctcgagta        60
ggtcaacgct cattgatagt accagagcag cttcagctac atgtccaggc aatgccgtag       120
cttgtgacag cata                                                         134

<210> SEQ ID NO 43
<211> LENGTH: 134
<212> TYPE: DNA
<213> ORGANISM: Artificial Sequence
<220> FEATURE:
<223> OTHER INFORMATION: Synthesized

<400> SEQUENCE: 43
agctatacgg agcatcgtga gattagtcaa ctagcctcgc atgtgtataa gcctcgagta        60
gagaggtgac tcatgatagt accagagcca gaacgactac atgtccaggc aatgccgtag       120
cttgtgacag cata                                                         134

<210> SEQ ID NO 44
<211> LENGTH: 134
```

```
<212> TYPE: DNA
<213> ORGANISM: Artificial Sequence
<220> FEATURE:
<223> OTHER INFORMATION: Synthesized

<400> SEQUENCE: 44
agctatacgg agcatcgtga gattagtcaa ctagcctcgc atgtgtataa gcctcgagta        60
gagagacacc atctgatagt accagagcag catcgactac atgtccaggc aatgccgtag       120
cttgtgacag cata                                                          134

<210> SEQ ID NO 45
<211> LENGTH: 134
<212> TYPE: DNA
<213> ORGANISM: Artificial Sequence
<220> FEATURE:
<223> OTHER INFORMATION: Synthesized

<400> SEQUENCE: 45
agctatacgg agcatcgtga gattagtcaa ctagcctcgc atgtgtataa gcctcgagta        60
gtctgatcga gcatgatagt accagagctg atgctgctac atgtccaggc aatgccgtag       120
cttgtgacag cata                                                          134

<210> SEQ ID NO 46
<211> LENGTH: 134
<212> TYPE: DNA
<213> ORGANISM: Artificial Sequence
<220> FEATURE:
<223> OTHER INFORMATION: Synthesized

<400> SEQUENCE: 46
agctatacgg agcatcgtga gattagtcaa ctagcctcgc atgtgtataa gcctcgagta        60
gtatggatcc gtatgatagt accagagcga tcctgactac atgtccaggc aatgccgtag       120
cttgtgacag cata                                                          134

<210> SEQ ID NO 47
<211> LENGTH: 134
<212> TYPE: DNA
<213> ORGANISM: Artificial Sequence
<220> FEATURE:
<223> OTHER INFORMATION: Synthesized

<400> SEQUENCE: 47
agctatacgg agcatcgtga gattagtcaa ctagcctcgc atgtgtataa gcctcgagta        60
ggacgtacgg agatgatagt accagagcac atcgctctac atgtccaggc aatgccgtag       120
cttgtgacag cata                                                          134

<210> SEQ ID NO 48
<211> LENGTH: 134
<212> TYPE: DNA
<213> ORGANISM: Artificial Sequence
<220> FEATURE:
<223> OTHER INFORMATION: Synthesized

<400> SEQUENCE: 48
agctatacgg agcatcgtga gattagtcaa ctagcctcgc atgtgtataa gcctcgagta        60
ggtaccacta tgttgatagt accagagcga tgagtgctac atgtccaggc aatgccgtag       120
cttgtgacag cata                                                          134

<210> SEQ ID NO 49
```

```
<211> LENGTH: 134
<212> TYPE: DNA
<213> ORGANISM: Artificial Sequence
<220> FEATURE:
<223> OTHER INFORMATION: Synthesized

<400> SEQUENCE: 49
agctatacgg agcatcgtga gattagtcaa ctagcctcgc atgtgtataa gcctcgagta      60
gctgccactc tactgatagt accagagcag cttcagctac atgtccaggc aatgccgtag     120
cttgtgacag cata                                                       134

<210> SEQ ID NO 50
<211> LENGTH: 134
<212> TYPE: DNA
<213> ORGANISM: Artificial Sequence
<220> FEATURE:
<223> OTHER INFORMATION: Synthesized

<400> SEQUENCE: 50
agctatacgg agcatcgtga gattagtcaa ctagcctcgc atgtgtataa gcctcgagta      60
gagaggtgac tcatgatagt accagagcct agctcactac atgtccaggc aatgccgtag     120
cttgtgacag cata                                                       134

<210> SEQ ID NO 51
<211> LENGTH: 134
<212> TYPE: DNA
<213> ORGANISM: Artificial Sequence
<220> FEATURE:
<223> OTHER INFORMATION: Synthesized

<400> SEQUENCE: 51
agctatacgg agcatcgtga gattagtcaa ctagcctcgc atgtgtataa gcctcgagta      60
gacacatgac agatgatagt accagagcct acacagctac atgtccaggc aatgccgtag     120
cttgtgacag cata                                                       134

<210> SEQ ID NO 52
<211> LENGTH: 134
<212> TYPE: DNA
<213> ORGANISM: Artificial Sequence
<220> FEATURE:
<223> OTHER INFORMATION: Synthesized

<400> SEQUENCE: 52
agctatacgg agcatcgtga gattagtcaa ctagcctcgc atgtgtataa gcctcgagta      60
gtgagctcga tgttgatagt accagagcta gccactctac atgtccaggc aatgccgtag     120
cttgtgacag cata                                                       134

<210> SEQ ID NO 53
<211> LENGTH: 134
<212> TYPE: DNA
<213> ORGANISM: Artificial Sequence
<220> FEATURE:
<223> OTHER INFORMATION: Synthesized

<400> SEQUENCE: 53
agctatacgg agcatcgtga gattagtcaa ctagcctcgc atgtgtataa gcctcgagta      60
gtatggatcc gtatgatagt accagagcag tgatgcctac atgtccaggc aatgccgtag     120
cttgtgacag cata                                                       134
```

-continued

```
<210> SEQ ID NO 54
<211> LENGTH: 134
<212> TYPE: DNA
<213> ORGANISM: Artificial Sequence
<220> FEATURE:
<223> OTHER INFORMATION: Synthesized

<400> SEQUENCE: 54
agctatacgg agcatcgtga gattagtcaa ctagcctcgc atgtgtataa gcctcgagta      60
ggtgcactgt cactgatagt accagagcca tcatgcctac atgtccaggc aatgccgtag     120
cttgtgacag cata                                                        134

<210> SEQ ID NO 55
<211> LENGTH: 134
<212> TYPE: DNA
<213> ORGANISM: Artificial Sequence
<220> FEATURE:
<223> OTHER INFORMATION: Synthesized

<400> SEQUENCE: 55
agctatacgg agcatcgtga gattagtcaa ctagcctcgc atgtgtataa gcctcgagta      60
ggtcaacgct cattgatagt accagagctg caacgtctac atgtccaggc aatgccgtag     120
cttgtgacag cata                                                        134

<210> SEQ ID NO 56
<211> LENGTH: 134
<212> TYPE: DNA
<213> ORGANISM: Artificial Sequence
<220> FEATURE:
<223> OTHER INFORMATION: Synthesized

<400> SEQUENCE: 56
agctatacgg agcatcgtga gattagtcaa ctagcctcac acctctataa gcctcgagta      60
ggtctatgac tcatgatagt accagagcca gaacgactac atgtccaggc aatgccgtag     120
cttgtgacag cata                                                        134

<210> SEQ ID NO 57
<211> LENGTH: 134
<212> TYPE: DNA
<213> ORGANISM: Artificial Sequence
<220> FEATURE:
<223> OTHER INFORMATION: Synthesized

<400> SEQUENCE: 57
agctatacgg agcatcgtga gattagtcaa ctagcctcac acctctataa gcctcgagta      60
gctagcagat cactgatagt accagagcag catcgactac atgtccaggc aatgccgtag     120
cttgtgacag cata                                                        134

<210> SEQ ID NO 58
<211> LENGTH: 134
<212> TYPE: DNA
<213> ORGANISM: Artificial Sequence
<220> FEATURE:
<223> OTHER INFORMATION: Synthesized

<400> SEQUENCE: 58
agctatacgg agcatcgtga gattagtcaa ctagcctcac acctctataa gcctcgagta      60
gtctagtagg atctgatagt accagagctg atgctgctac atgtccaggc aatgccgtag     120
cttgtgacag cata                                                        134
```

-continued

```
<210> SEQ ID NO 59
<211> LENGTH: 134
<212> TYPE: DNA
<213> ORGANISM: Artificial Sequence
<220> FEATURE:
<223> OTHER INFORMATION: Synthesized

<400> SEQUENCE: 59
agctatacgg agcatcgtga gattagtcaa ctagcctcac acctctataa gcctcgagta        60
ggataagcag agttgatagt accagagcga tcctgactac atgtccaggc aatgccgtag       120
cttgtgacag cata                                                        134

<210> SEQ ID NO 60
<211> LENGTH: 134
<212> TYPE: DNA
<213> ORGANISM: Artificial Sequence
<220> FEATURE:
<223> OTHER INFORMATION: Synthesized

<400> SEQUENCE: 60
agctatacgg agcatcgtga gattagtcaa ctagcctcac acctctataa gcctcgagta        60
gagcacacac acttgatagt accagagcac atcgctctac atgtccaggc aatgccgtag       120
cttgtgacag cata                                                        134

<210> SEQ ID NO 61
<211> LENGTH: 134
<212> TYPE: DNA
<213> ORGANISM: Artificial Sequence
<220> FEATURE:
<223> OTHER INFORMATION: Synthesized

<400> SEQUENCE: 61
agctatacgg agcatcgtga gattagtcaa ctagcctcac acctctataa gcctcgagta        60
gtcgtgtcgg ctatgatagt accagagcga tgagtgctac atgtccaggc aatgccgtag       120
cttgtgacag cata                                                        134

<210> SEQ ID NO 62
<211> LENGTH: 134
<212> TYPE: DNA
<213> ORGANISM: Artificial Sequence
<220> FEATURE:
<223> OTHER INFORMATION: Synthesized

<400> SEQUENCE: 62
agctatacgg agcatcgtga gattagtcaa ctagcctcac acctctataa gcctcgagta        60
gtatgagtgg tgctgatagt accagagcag cttcagctac atgtccaggc aatgccgtag       120
cttgtgacag cata                                                        134

<210> SEQ ID NO 63
<211> LENGTH: 134
<212> TYPE: DNA
<213> ORGANISM: Artificial Sequence
<220> FEATURE:
<223> OTHER INFORMATION: Synthesized

<400> SEQUENCE: 63
agctatacgg agcatcgtga gattagtcaa ctagcctcac acctctataa gcctcgagta        60
gcacggtctc gattgatagt accagagcct agctcactac atgtccaggc aatgccgtag       120
cttgtgacag cata                                                        134
```

```
<210> SEQ ID NO 64
<211> LENGTH: 134
<212> TYPE: DNA
<213> ORGANISM: Artificial Sequence
<220> FEATURE:
<223> OTHER INFORMATION: Synthesized

<400> SEQUENCE: 64
agctatacgg agcatcgtga gattagtcaa ctagcctcac acctctataa gcctcgagta      60
ggctatcagg atatgatagt accagagcct acacagctac atgtccaggc aatgccgtag     120
cttgtgacag cata                                                       134

<210> SEQ ID NO 65
<211> LENGTH: 134
<212> TYPE: DNA
<213> ORGANISM: Artificial Sequence
<220> FEATURE:
<223> OTHER INFORMATION: Synthesized

<400> SEQUENCE: 65
agctatacgg agcatcgtga gattagtcaa ctagcctcac acctctataa gcctcgagta      60
gatgtactcc acgtgatagt accagagcta gccactctac atgtccaggc aatgccgtag     120
cttgtgacag cata                                                       134

<210> SEQ ID NO 66
<211> LENGTH: 134
<212> TYPE: DNA
<213> ORGANISM: Artificial Sequence
<220> FEATURE:
<223> OTHER INFORMATION: Synthesized

<400> SEQUENCE: 66
agctatacgg agcatcgtga gattagtcaa ctagcctcac acctctataa gcctcgagta      60
gtagactgaa cgttgatagt accagagcag tgatgcctac atgtccaggc aatgccgtag     120
cttgtgacag cata                                                       134

<210> SEQ ID NO 67
<211> LENGTH: 134
<212> TYPE: DNA
<213> ORGANISM: Artificial Sequence
<220> FEATURE:
<223> OTHER INFORMATION: Synthesized

<400> SEQUENCE: 67
agctatacgg agcatcgtga gattagtcaa ctagcctcac acctctataa gcctcgagta      60
ggagctctgc tgatgatagt accagagcca tcatgcctac atgtccaggc aatgccgtag     120
cttgtgacag cata                                                       134

<210> SEQ ID NO 68
<211> LENGTH: 134
<212> TYPE: DNA
<213> ORGANISM: Artificial Sequence
<220> FEATURE:
<223> OTHER INFORMATION: Synthesized

<400> SEQUENCE: 68
agctatacgg agcatcgtga gattagtcaa ctagcctcac acctctataa gcctcgagta      60
gtcaccactt ctatgatagt accagagctg caacgtctac atgtccaggc aatgccgtag     120
```

```
cttgtgacag cata                                              134
```

```
<210> SEQ ID NO 69
<211> LENGTH: 134
<212> TYPE: DNA
<213> ORGANISM: Artificial Sequence
<220> FEATURE:
<223> OTHER INFORMATION: Synthesized

<400> SEQUENCE: 69
agctatacgg agcatcgtga gattagtcaa ctagcctcac acctctataa gcctcgagta      60
gcgcactcaa tagtgatagt accagagcac gcatcactac atgtccaggc aatgccgtag     120
cttgtgacag cata                                              134

<210> SEQ ID NO 70
<211> LENGTH: 134
<212> TYPE: DNA
<213> ORGANISM: Artificial Sequence
<220> FEATURE:
<223> OTHER INFORMATION: Synthesized

<400> SEQUENCE: 70
agctatacgg agcatcgtga gattagtcaa ctagcctcac acctctataa gcctcgagta      60
gtatctacga ctgtgatagt accagagcgt gatgctctac atgtccaggc aatgccgtag     120
cttgtgacag cata                                              134

<210> SEQ ID NO 71
<211> LENGTH: 134
<212> TYPE: DNA
<213> ORGANISM: Artificial Sequence
<220> FEATURE:
<223> OTHER INFORMATION: Synthesized

<400> SEQUENCE: 71
agctatacgg agcatcgtga gattagtcaa ctagcctcac acctctataa gcctcgagta      60
gcacacatct agttgatagt accagagctg acctagctac atgtccaggc aatgccgtag     120
cttgtgacag cata                                              134

<210> SEQ ID NO 72
<211> LENGTH: 134
<212> TYPE: DNA
<213> ORGANISM: Artificial Sequence
<220> FEATURE:
<223> OTHER INFORMATION: Synthesized

<400> SEQUENCE: 72
agctatacgg agcatcgtga gattagtcaa ctagcctcac acctctataa gcctcgagta      60
ggtcaacgct cattgatagt accagagctg tcacacctac atgtccaggc aatgccgtag     120
cttgtgacag cata                                              134

<210> SEQ ID NO 73
<211> LENGTH: 134
<212> TYPE: DNA
<213> ORGANISM: Artificial Sequence
<220> FEATURE:
<223> OTHER INFORMATION: Synthesized

<400> SEQUENCE: 73
agctatacgg agcatcgtga gattagtcaa ctagcctcca gagtacataa gcctcgagta      60
gtatgtatcg ctctgatagt accagagcca gaacgactac atgtccaggc aatgccgtag     120
```

-continued

```
cttgtgacag cata                                                        134

<210> SEQ ID NO 74
<211> LENGTH: 134
<212> TYPE: DNA
<213> ORGANISM: Artificial Sequence
<220> FEATURE:
<223> OTHER INFORMATION: Synthesized

<400> SEQUENCE: 74
agctatacgg agcatcgtga gattagtcaa ctagcctcca gagtacataa gcctcgagta      60
gtgacctcgt gtctgatagt accagagcag catcgactac atgtccaggc aatgccgtag     120
cttgtgacag cata                                                        134

<210> SEQ ID NO 75
<211> LENGTH: 134
<212> TYPE: DNA
<213> ORGANISM: Artificial Sequence
<220> FEATURE:
<223> OTHER INFORMATION: Synthesized

<400> SEQUENCE: 75
agctatacgg agcatcgtga gattagtcaa ctagcctcca gagtacataa gcctcgagta      60
gcgtggtacg tactgatagt accagagctg atgctgctac atgtccaggc aatgccgtag     120
cttgtgacag cata                                                        134

<210> SEQ ID NO 76
<211> LENGTH: 134
<212> TYPE: DNA
<213> ORGANISM: Artificial Sequence
<220> FEATURE:
<223> OTHER INFORMATION: Synthesized

<400> SEQUENCE: 76
agctatacgg agcatcgtga gattagtcaa ctagcctcca gagtacataa gcctcgagta      60
gactgctctc gtgtgatagt accagagcga tcctgactac atgtccaggc aatgccgtag     120
cttgtgacag cata                                                        134

<210> SEQ ID NO 77
<211> LENGTH: 134
<212> TYPE: DNA
<213> ORGANISM: Artificial Sequence
<220> FEATURE:
<223> OTHER INFORMATION: Synthesized

<400> SEQUENCE: 77
agctatacgg agcatcgtga gattagtcaa ctagcctcca gagtacataa gcctcgagta      60
gtctcgcaca gcatgatagt accagagcac atcgctctac atgtccaggc aatgccgtag     120
cttgtgacag cata                                                        134

<210> SEQ ID NO 78
<211> LENGTH: 134
<212> TYPE: DNA
<213> ORGANISM: Artificial Sequence
<220> FEATURE:
<223> OTHER INFORMATION: Synthesized

<400> SEQUENCE: 78
agctatacgg agcatcgtga gattagtcaa ctagcctcca gagtacataa gcctcgagta      60
```

```
ggcgtactag agttgatagt accagagcga tgagtgctac atgtccaggc aatgccgtag      120
cttgtgacag cata                                                        134

<210> SEQ ID NO 79
<211> LENGTH: 134
<212> TYPE: DNA
<213> ORGANISM: Artificial Sequence
<220> FEATURE:
<223> OTHER INFORMATION: Synthesized

<400> SEQUENCE: 79
agctatacgg agcatcgtga gattagtcaa ctagcctcca gagtacataa gcctcgagta       60
gtatgcagtg acatgatagt accagagcag cttcagctac atgtccaggc aatgccgtag      120
cttgtgacag cata                                                        134

<210> SEQ ID NO 80
<211> LENGTH: 134
<212> TYPE: DNA
<213> ORGANISM: Artificial Sequence
<220> FEATURE:
<223> OTHER INFORMATION: Synthesized

<400> SEQUENCE: 80
agctatacgg agcatcgtga gattagtcaa ctagcctcca gagtacataa gcctcgagta       60
gcacggtctc gattgatagt accagagcct agctcactac atgtccaggc aatgccgtag      120
cttgtgacag cata                                                        134

<210> SEQ ID NO 81
<211> LENGTH: 134
<212> TYPE: DNA
<213> ORGANISM: Artificial Sequence
<220> FEATURE:
<223> OTHER INFORMATION: Synthesized

<400> SEQUENCE: 81
agctatacgg agcatcgtga gattagtcaa ctagcctcca gagtacataa gcctcgagta       60
gagtcacagt gattgatagt accagagcct acacagctac atgtccaggc aatgccgtag      120
cttgtgacag cata                                                        134

<210> SEQ ID NO 82
<211> LENGTH: 134
<212> TYPE: DNA
<213> ORGANISM: Artificial Sequence
<220> FEATURE:
<223> OTHER INFORMATION: Synthesized

<400> SEQUENCE: 82
agctatacgg agcatcgtga gattagtcaa ctagcctcca gagtacataa gcctcgagta       60
ggatgacgat ctatgatagt accagagcta gccactctac atgtccaggc aatgccgtag      120
cttgtgacag cata                                                        134

<210> SEQ ID NO 83
<211> LENGTH: 134
<212> TYPE: DNA
<213> ORGANISM: Artificial Sequence
<220> FEATURE:
<223> OTHER INFORMATION: Synthesized

<400> SEQUENCE: 83
agctatacgg agcatcgtga gattagtcaa ctagcctcca gagtacataa gcctcgagta       60
```

```
gatgcgtagc gtatgatagt accagagcag tgatgcctac atgtccaggc aatgccgtag        120
cttgtgacag cata                                                          134

<210> SEQ ID NO 84
<211> LENGTH: 134
<212> TYPE: DNA
<213> ORGANISM: Artificial Sequence
<220> FEATURE:
<223> OTHER INFORMATION: Synthesized

<400> SEQUENCE: 84
agctatacgg agcatcgtga gattagtcaa ctagcctcca gagtacataa gcctcgagta         60
gagctgcagg atctgatagt accagagcca tcatgcctac atgtccaggc aatgccgtag        120
cttgtgacag cata                                                          134

<210> SEQ ID NO 85
<211> LENGTH: 134
<212> TYPE: DNA
<213> ORGANISM: Artificial Sequence
<220> FEATURE:
<223> OTHER INFORMATION: Synthesized

<400> SEQUENCE: 85
agctatacgg agcatcgtga gattagtcaa ctagcctcca gagtacataa gcctcgagta         60
gtgagtatac gactgatagt accagagctg caacgtctac atgtccaggc aatgccgtag        120
cttgtgacag cata                                                          134

<210> SEQ ID NO 86
<211> LENGTH: 134
<212> TYPE: DNA
<213> ORGANISM: Artificial Sequence
<220> FEATURE:
<223> OTHER INFORMATION: Synthesized

<400> SEQUENCE: 86
agctatacgg agcatcgtga gattagtcaa ctagcctcca gagtacataa gcctcgagta         60
ggtgcatgcg tcttgatagt accagagcac gcatcactac atgtccaggc aatgccgtag        120
cttgtgacag cata                                                          134

<210> SEQ ID NO 87
<211> LENGTH: 134
<212> TYPE: DNA
<213> ORGANISM: Artificial Sequence
<220> FEATURE:
<223> OTHER INFORMATION: Synthesized

<400> SEQUENCE: 87
agctatacgg agcatcgtga gattagtcaa ctagcctcca gagtacataa gcctcgagta         60
gctcacacta cattgatagt accagagcgt gatgctctac atgtccaggc aatgccgtag        120
cttgtgacag cata                                                          134

<210> SEQ ID NO 88
<211> LENGTH: 134
<212> TYPE: DNA
<213> ORGANISM: Artificial Sequence
<220> FEATURE:
<223> OTHER INFORMATION: Synthesized

<400> SEQUENCE: 88
```

```
agctatacgg agcatcgtga gattagtcaa ctagcctcca gagtacataa gcctcgagta      60
gcacacatct agttgatagt accagagctg acctagctac atgtccaggc aatgccgtag     120
cttgtgacag cata                                                       134

<210> SEQ ID NO 89
<211> LENGTH: 134
<212> TYPE: DNA
<213> ORGANISM: Artificial Sequence
<220> FEATURE:
<223> OTHER INFORMATION: Synthesized

<400> SEQUENCE: 89
agctatacgg agcatcgtga gattagtcaa ctagcctcca gagtacataa gcctcgagta      60
ggtcaacgct cattgatagt accagagctg tcacacctac atgtccaggc aatgccgtag     120
cttgtgacag cata                                                       134

<210> SEQ ID NO 90
<211> LENGTH: 134
<212> TYPE: DNA
<213> ORGANISM: Artificial Sequence
<220> FEATURE:
<223> OTHER INFORMATION: Synthesized

<400> SEQUENCE: 90
agctatacgg agcatcgtga gattagtcaa ctagcctcac tgagtcataa gcctcgagta      60
gtgtagcgtg atatgatagt accagagcca gaacgactac atgtccaggc aatgccgtag     120
cttgtgacag cata                                                       134

<210> SEQ ID NO 91
<211> LENGTH: 134
<212> TYPE: DNA
<213> ORGANISM: Artificial Sequence
<220> FEATURE:
<223> OTHER INFORMATION: Synthesized

<400> SEQUENCE: 91
agctatacgg agcatcgtga gattagtcaa ctagcctcac tgagtcataa gcctcgagta      60
gctcgagtgt atatgatagt accagagcag catcgactac atgtccaggc aatgccgtag     120
cttgtgacag cata                                                       134

<210> SEQ ID NO 92
<211> LENGTH: 134
<212> TYPE: DNA
<213> ORGANISM: Artificial Sequence
<220> FEATURE:
<223> OTHER INFORMATION: Synthesized

<400> SEQUENCE: 92
agctatacgg agcatcgtga gattagtcaa ctagcctcac tgagtcataa gcctcgagta      60
gtactactgc gtctgatagt accagagctg atgctgctac atgtccaggc aatgccgtag     120
cttgtgacag cata                                                       134

<210> SEQ ID NO 93
<211> LENGTH: 134
<212> TYPE: DNA
<213> ORGANISM: Artificial Sequence
<220> FEATURE:
<223> OTHER INFORMATION: Synthesized

<400> SEQUENCE: 93
```

```
agctatacgg agcatcgtga gattagtcaa ctagcctcac tgagtcataa gcctcgagta      60
gtgtggtgtg tactgatagt accagagcga tcctgactac atgtccaggc aatgccgtag     120
cttgtgacag cata                                                       134

<210> SEQ ID NO 94
<211> LENGTH: 134
<212> TYPE: DNA
<213> ORGANISM: Artificial Sequence
<220> FEATURE:
<223> OTHER INFORMATION: Synthesized

<400> SEQUENCE: 94
agctatacgg agcatcgtga gattagtcaa ctagcctcac tgagtcataa gcctcgagta      60
ggcgacactg atatgatagt accagagcac atcgctctac atgtccaggc aatgccgtag     120
cttgtgacag cata                                                       134

<210> SEQ ID NO 95
<211> LENGTH: 134
<212> TYPE: DNA
<213> ORGANISM: Artificial Sequence
<220> FEATURE:
<223> OTHER INFORMATION: Synthesized

<400> SEQUENCE: 95
agctatacgg agcatcgtga gattagtcaa ctagcctcac tgagtcataa gcctcgagta      60
ggcgagatat agatgatagt accagagcga tgagtgctac atgtccaggc aatgccgtag     120
cttgtgacag cata                                                       134

<210> SEQ ID NO 96
<211> LENGTH: 134
<212> TYPE: DNA
<213> ORGANISM: Artificial Sequence
<220> FEATURE:
<223> OTHER INFORMATION: Synthesized

<400> SEQUENCE: 96
agctatacgg agcatcgtga gattagtcaa ctagcctcac tgagtcataa gcctcgagta      60
gctgtgctgc acatgatagt accagagcag cttcagctac atgtccaggc aatgccgtag     120
cttgtgacag cata                                                       134

<210> SEQ ID NO 97
<211> LENGTH: 134
<212> TYPE: DNA
<213> ORGANISM: Artificial Sequence
<220> FEATURE:
<223> OTHER INFORMATION: Synthesized

<400> SEQUENCE: 97
agctatacgg agcatcgtga gattagtcaa ctagcctcac tgagtcataa gcctcgagta      60
gcacggtctc gattgatagt accagagcct agctcactac atgtccaggc aatgccgtag     120
cttgtgacag cata                                                       134

<210> SEQ ID NO 98
<211> LENGTH: 134
<212> TYPE: DNA
<213> ORGANISM: Artificial Sequence
<220> FEATURE:
<223> OTHER INFORMATION: Synthesized
```

-continued

```
<400> SEQUENCE: 98
agctatacgg agcatcgtga gattagtcaa ctagcctcac tgagtcataa gcctcgagta      60
gtgacactca cagtgatagt accagagcct acacagctac atgtccaggc aatgccgtag     120
cttgtgacag cata                                                        134

<210> SEQ ID NO 99
<211> LENGTH: 134
<212> TYPE: DNA
<213> ORGANISM: Artificial Sequence
<220> FEATURE:
<223> OTHER INFORMATION: Synthesized

<400> SEQUENCE: 99
agctatacgg agcatcgtga gattagtcaa ctagcctcac tgagtcataa gcctcgagta      60
gtatgtagct gcgtgatagt accagagcta gccactctac atgtccaggc aatgccgtag     120
cttgtgacag cata                                                        134

<210> SEQ ID NO 100
<211> LENGTH: 134
<212> TYPE: DNA
<213> ORGANISM: Artificial Sequence
<220> FEATURE:
<223> OTHER INFORMATION: Synthesized

<400> SEQUENCE: 100
agctatacgg agcatcgtga gattagtcaa ctagcctcac tgagtcataa gcctcgagta      60
gcatccatgc tgatgatagt accagagcag tgatgcctac atgtccaggc aatgccgtag     120
cttgtgacag cata                                                        134

<210> SEQ ID NO 101
<211> LENGTH: 134
<212> TYPE: DNA
<213> ORGANISM: Artificial Sequence
<220> FEATURE:
<223> OTHER INFORMATION: Synthesized

<400> SEQUENCE: 101
agctatacgg agcatcgtga gattagtcaa ctagcctcac tgagtcataa gcctcgagta      60
gcgacgagcc atatgatagt accagagcca tcatgcctac atgtccaggc aatgccgtag     120
cttgtgacag cata                                                        134

<210> SEQ ID NO 102
<211> LENGTH: 134
<212> TYPE: DNA
<213> ORGANISM: Artificial Sequence
<220> FEATURE:
<223> OTHER INFORMATION: Synthesized

<400> SEQUENCE: 102
agctatacgg agcatcgtga gattagtcaa ctagcctcac tgagtcataa gcctcgagta      60
gcgatgtgtt acttgatagt accagagctg caacgtctac atgtccaggc aatgccgtag     120
cttgtgacag cata                                                        134

<210> SEQ ID NO 103
<211> LENGTH: 134
<212> TYPE: DNA
<213> ORGANISM: Artificial Sequence
<220> FEATURE:
<223> OTHER INFORMATION: Synthesized
```

<400> SEQUENCE: 103
agctatacgg agcatcgtga gattagtcaa ctagcctcac tgagtcataa gcctcgagta      60
gacatctcgt cactgatagt accagagcac gcatcactac atgtccaggc aatgccgtag     120
cttgtgacag cata                                                       134

<210> SEQ ID NO 104
<211> LENGTH: 134
<212> TYPE: DNA
<213> ORGANISM: Artificial Sequence
<220> FEATURE:
<223> OTHER INFORMATION: Synthesized

<400> SEQUENCE: 104
agctatacgg agcatcgtga gattagtcaa ctagcctcac tgagtcataa gcctcgagta      60
ggtgctacat agttgatagt accagagcgt gatgctctac atgtccaggc aatgccgtag     120
cttgtgacag cata                                                       134

<210> SEQ ID NO 105
<211> LENGTH: 134
<212> TYPE: DNA
<213> ORGANISM: Artificial Sequence
<220> FEATURE:
<223> OTHER INFORMATION: Synthesized

<400> SEQUENCE: 105
agctatacgg agcatcgtga gattagtcaa ctagcctcac tgagtcataa gcctcgagta      60
gcacacatct agttgatagt accagagctg acctagctac atgtccaggc aatgccgtag     120
cttgtgacag cata                                                       134

<210> SEQ ID NO 106
<211> LENGTH: 134
<212> TYPE: DNA
<213> ORGANISM: Artificial Sequence
<220> FEATURE:
<223> OTHER INFORMATION: Synthesized

<400> SEQUENCE: 106
agctatacgg agcatcgtga gattagtcaa ctagcctcac tgagtcataa gcctcgagta      60
ggtcaacgct cattgatagt accagagctg tcacacctac atgtccaggc aatgccgtag     120
cttgtgacag cata                                                       134

<210> SEQ ID NO 107
<211> LENGTH: 134
<212> TYPE: DNA
<213> ORGANISM: Artificial Sequence
<220> FEATURE:
<223> OTHER INFORMATION: Synthesized

<400> SEQUENCE: 107
agctatacgg agcatcgtga gattagtcaa ctagcctcct acgatgataa gcctcgagta      60
gataggcatc gactgatagt accagagcca gaacgactac atgtccaggc aatgccgtag     120
cttgtgacag cata                                                       134

<210> SEQ ID NO 108
<211> LENGTH: 134
<212> TYPE: DNA
<213> ORGANISM: Artificial Sequence
<220> FEATURE:

-continued

```
<223> OTHER INFORMATION: Synthesized

<400> SEQUENCE: 108
agctatacgg agcatcgtga gattagtcaa ctagcctcct acgatgataa gcctcgagta       60
gagatcacgg cagtgatagt accagagcag catcgactac atgtccaggc aatgccgtag      120
cttgtgacag cata                                                        134

<210> SEQ ID NO 109
<211> LENGTH: 134
<212> TYPE: DNA
<213> ORGANISM: Artificial Sequence
<220> FEATURE:
<223> OTHER INFORMATION: Synthesized

<400> SEQUENCE: 109
agctatacgg agcatcgtga gattagtcaa ctagcctcct acgatgataa gcctcgagta       60
gagtcgagaa tcttgatagt accagagctg atgctgctac atgtccaggc aatgccgtag      120
cttgtgacag cata                                                        134

<210> SEQ ID NO 110
<211> LENGTH: 134
<212> TYPE: DNA
<213> ORGANISM: Artificial Sequence
<220> FEATURE:
<223> OTHER INFORMATION: Synthesized

<400> SEQUENCE: 110
agctatacgg agcatcgtga gattagtcaa ctagcctcct acgatgataa gcctcgagta       60
gtagcgagct cattgatagt accagagcga tcctgactac atgtccaggc aatgccgtag      120
cttgtgacag cata                                                        134

<210> SEQ ID NO 111
<211> LENGTH: 134
<212> TYPE: DNA
<213> ORGANISM: Artificial Sequence
<220> FEATURE:
<223> OTHER INFORMATION: Synthesized

<400> SEQUENCE: 111
agctatacgg agcatcgtga gattagtcaa ctagcctcct acgatgataa gcctcgagta       60
ggcgacagtt acatgatagt accagagcac atcgctctac atgtccaggc aatgccgtag      120
cttgtgacag cata                                                        134

<210> SEQ ID NO 112
<211> LENGTH: 134
<212> TYPE: DNA
<213> ORGANISM: Artificial Sequence
<220> FEATURE:
<223> OTHER INFORMATION: Synthesized

<400> SEQUENCE: 112
agctatacgg agcatcgtga gattagtcaa ctagcctcct acgatgataa gcctcgagta       60
gatcgatctt ctctgatagt accagagcga tgagtgctac atgtccaggc aatgccgtag      120
cttgtgacag cata                                                        134

<210> SEQ ID NO 113
<211> LENGTH: 134
<212> TYPE: DNA
<213> ORGANISM: Artificial Sequence
```

-continued

```
<220> FEATURE:
<223> OTHER INFORMATION: Synthesized

<400> SEQUENCE: 113
agctatacgg agcatcgtga gattagtcaa ctagcctcct acgatgataa gcctcgagta      60
gagcacagaa ctgtgatagt accagagcag cttcagctac atgtccaggc aatgccgtag     120
cttgtgacag cata                                                        134

<210> SEQ ID NO 114
<211> LENGTH: 134
<212> TYPE: DNA
<213> ORGANISM: Artificial Sequence
<220> FEATURE:
<223> OTHER INFORMATION: Synthesized

<400> SEQUENCE: 114
agctatacgg agcatcgtga gattagtcaa ctagcctcct acgatgataa gcctcgagta      60
gcacggtctc gattgatagt accagagcct agctcactac atgtccaggc aatgccgtag     120
cttgtgacag cata                                                        134

<210> SEQ ID NO 115
<211> LENGTH: 134
<212> TYPE: DNA
<213> ORGANISM: Artificial Sequence
<220> FEATURE:
<223> OTHER INFORMATION: Synthesized

<400> SEQUENCE: 115
agctatacgg agcatcgtga gattagtcaa ctagcctcct acgatgataa gcctcgagta      60
gcagctgact cactgatagt accagagcct acacagctac atgtccaggc aatgccgtag     120
cttgtgacag cata                                                        134

<210> SEQ ID NO 116
<211> LENGTH: 134
<212> TYPE: DNA
<213> ORGANISM: Artificial Sequence
<220> FEATURE:
<223> OTHER INFORMATION: Synthesized

<400> SEQUENCE: 116
agctatacgg agcatcgtga gattagtcaa ctagcctcct acgatgataa gcctcgagta      60
gcagcctgac atgtgatagt accagagcta gccactctac atgtccaggc aatgccgtag     120
cttgtgacag cata                                                        134

<210> SEQ ID NO 117
<211> LENGTH: 134
<212> TYPE: DNA
<213> ORGANISM: Artificial Sequence
<220> FEATURE:
<223> OTHER INFORMATION: Synthesized

<400> SEQUENCE: 117
agctatacgg agcatcgtga gattagtcaa ctagcctcct acgatgataa gcctcgagta      60
gactctgcat cattgatagt accagagcag tgatgcctac atgtccaggc aatgccgtag     120
cttgtgacag cata                                                        134

<210> SEQ ID NO 118
<211> LENGTH: 134
<212> TYPE: DNA
```

-continued

<213> ORGANISM: Artificial Sequence
<220> FEATURE:
<223> OTHER INFORMATION: Synthesized

<400> SEQUENCE: 118

```
agctatacgg agcatcgtga gattagtcaa ctagcctcct acgatgataa gcctcgagta      60
gtcatagcga tcttgatagt accagagcca tcatgcctac atgtccaggc aatgccgtag     120
cttgtgacag cata                                                       134
```

<210> SEQ ID NO 119
<211> LENGTH: 134
<212> TYPE: DNA
<213> ORGANISM: Artificial Sequence
<220> FEATURE:
<223> OTHER INFORMATION: Synthesized

<400> SEQUENCE: 119

```
agctatacgg agcatcgtga gattagtcaa ctagcctcct acgatgataa gcctcgagta      60
gtatcgctgt gtgtgatagt accagagctg caacgtctac atgtccaggc aatgccgtag     120
cttgtgacag cata                                                       134
```

<210> SEQ ID NO 120
<211> LENGTH: 134
<212> TYPE: DNA
<213> ORGANISM: Artificial Sequence
<220> FEATURE:
<223> OTHER INFORMATION: Synthesized

<400> SEQUENCE: 120

```
agctatacgg agcatcgtga gattagtcaa ctagcctcct acgatgataa gcctcgagta      60
ggtgacgcgt gtatgatagt accagagcac gcatcactac atgtccaggc aatgccgtag     120
cttgtgacag cata                                                       134
```

<210> SEQ ID NO 121
<211> LENGTH: 134
<212> TYPE: DNA
<213> ORGANISM: Artificial Sequence
<220> FEATURE:
<223> OTHER INFORMATION: Synthesized

<400> SEQUENCE: 121

```
agctatacgg agcatcgtga gattagtcaa ctagcctcct acgatgataa gcctcgagta      60
gcgcactgca tgatgatagt accagagcgt gatgctctac atgtccaggc aatgccgtag     120
cttgtgacag cata                                                       134
```

<210> SEQ ID NO 122
<211> LENGTH: 134
<212> TYPE: DNA
<213> ORGANISM: Artificial Sequence
<220> FEATURE:
<223> OTHER INFORMATION: Synthesized

<400> SEQUENCE: 122

```
agctatacgg agcatcgtga gattagtcaa ctagcctcct acgatgataa gcctcgagta      60
gcacacatct agttgatagt accagagctg acctagctac atgtccaggc aatgccgtag     120
cttgtgacag cata                                                       134
```

<210> SEQ ID NO 123
<211> LENGTH: 134

<212> TYPE: DNA
<213> ORGANISM: Artificial Sequence
<220> FEATURE:
<223> OTHER INFORMATION: Synthesized

<400> SEQUENCE: 123
agctatacgg agcatcgtga gattagtcaa ctagcctcct acgatgataa gcctcgagta      60
ggtcaacgct cattgatagt accagagctg tcacacctac atgtccaggc aatgccgtag     120
cttgtgacag cata                                                       134

<210> SEQ ID NO 124
<211> LENGTH: 134
<212> TYPE: DNA
<213> ORGANISM: Artificial Sequence
<220> FEATURE:
<223> OTHER INFORMATION: Synthesized

<400> SEQUENCE: 124
agctatacgg agcatcgtga gattagtcaa ctagcctcgc agatgtataa gcctcgagta      60
gcgacgagcc atatgatagt accagagcca gaacgactac atgtccaggc aatgccgtag     120
cttgtgacag cata                                                       134

<210> SEQ ID NO 125
<211> LENGTH: 134
<212> TYPE: DNA
<213> ORGANISM: Artificial Sequence
<220> FEATURE:
<223> OTHER INFORMATION: Synthesized

<400> SEQUENCE: 125
agctatacgg agcatcgtga gattagtcaa ctagcctcgc agatgtataa gcctcgagta      60
gctcagatgg cattgatagt accagagcag catcgactac atgtccaggc aatgccgtag     120
cttgtgacag cata                                                       134

<210> SEQ ID NO 126
<211> LENGTH: 134
<212> TYPE: DNA
<213> ORGANISM: Artificial Sequence
<220> FEATURE:
<223> OTHER INFORMATION: Synthesized

<400> SEQUENCE: 126
agctatacgg agcatcgtga gattagtcaa ctagcctcgc agatgtataa gcctcgagta      60
gactctagtg tgatgatagt accagagctg atgctgctac atgtccaggc aatgccgtag     120
cttgtgacag cata                                                       134

<210> SEQ ID NO 127
<211> LENGTH: 134
<212> TYPE: DNA
<213> ORGANISM: Artificial Sequence
<220> FEATURE:
<223> OTHER INFORMATION: Synthesized

<400> SEQUENCE: 127
agctatacgg agcatcgtga gattagtcaa ctagcctcgc agatgtataa gcctcgagta      60
gatatgtgcg tgttgatagt accagagcga tcctgactac atgtccaggc aatgccgtag     120
cttgtgacag cata                                                       134

<210> SEQ ID NO 128

```
<211> LENGTH: 134
<212> TYPE: DNA
<213> ORGANISM: Artificial Sequence
<220> FEATURE:
<223> OTHER INFORMATION: Synthesized

<400> SEQUENCE: 128
agctatacgg agcatcgtga gattagtcaa ctagcctcgc agatgtataa gcctcgagta        60
gcgacgagcc atatgatagt accagagcac atcgctctac atgtccaggc aatgccgtag       120
cttgtgacag cata                                                          134

<210> SEQ ID NO 129
<211> LENGTH: 134
<212> TYPE: DNA
<213> ORGANISM: Artificial Sequence
<220> FEATURE:
<223> OTHER INFORMATION: Synthesized

<400> SEQUENCE: 129
agctatacgg agcatcgtga gattagtcaa ctagcctcgc agatgtataa gcctcgagta        60
gctcagatgg cattgatagt accagagcga tgagtgctac atgtccaggc aatgccgtag       120
cttgtgacag cata                                                          134

<210> SEQ ID NO 130
<211> LENGTH: 134
<212> TYPE: DNA
<213> ORGANISM: Artificial Sequence
<220> FEATURE:
<223> OTHER INFORMATION: Synthesized

<400> SEQUENCE: 130
agctatacgg agcatcgtga gattagtcaa ctagcctcgc agatgtataa gcctcgagta        60
gactctagtg tgatgatagt accagagcag cttcagctac atgtccaggc aatgccgtag       120
cttgtgacag cata                                                          134

<210> SEQ ID NO 131
<211> LENGTH: 134
<212> TYPE: DNA
<213> ORGANISM: Artificial Sequence
<220> FEATURE:
<223> OTHER INFORMATION: Synthesized

<400> SEQUENCE: 131
agctatacgg agcatcgtga gattagtcaa ctagcctcgc agatgtataa gcctcgagta        60
gatatgtgcg tgttgatagt accagagcct agctcactac atgtccaggc aatgccgtag       120
cttgtgacag cata                                                          134

<210> SEQ ID NO 132
<211> LENGTH: 134
<212> TYPE: DNA
<213> ORGANISM: Artificial Sequence
<220> FEATURE:
<223> OTHER INFORMATION: Synthesized

<400> SEQUENCE: 132
agctatacgg agcatcgtga gattagtcaa ctagcctcgc agatgtataa gcctcgagta        60
gctcgctgta ctatgatagt accagagcct acacagctac atgtccaggc aatgccgtag       120
cttgtgacag cata                                                          134
```

<210> SEQ ID NO 133
<211> LENGTH: 134
<212> TYPE: DNA
<213> ORGANISM: Artificial Sequence
<220> FEATURE:
<223> OTHER INFORMATION: Synthesized

<400> SEQUENCE: 133
agctatacgg agcatcgtga gattagtcaa ctagcctcgc agatgtataa gcctcgagta      60
gacaggctga gcttgatagt accagagcta gccactctac atgtccaggc aatgccgtag     120
cttgtgacag cata                                                       134

<210> SEQ ID NO 134
<211> LENGTH: 134
<212> TYPE: DNA
<213> ORGANISM: Artificial Sequence
<220> FEATURE:
<223> OTHER INFORMATION: Synthesized

<400> SEQUENCE: 134
agctatacgg agcatcgtga gattagtcaa ctagcctcgc agatgtataa gcctcgagta      60
gctcagatgg cattgatagt accagagcag tgatgcctac atgtccaggc aatgccgtag     120
cttgtgacag cata                                                       134

<210> SEQ ID NO 135
<211> LENGTH: 134
<212> TYPE: DNA
<213> ORGANISM: Artificial Sequence
<220> FEATURE:
<223> OTHER INFORMATION: Synthesized

<400> SEQUENCE: 135
agctatacgg agcatcgtga gattagtcaa ctagcctcgc agatgtataa gcctcgagta      60
gcacggtctc gattgatagt accagagcca tcatgcctac atgtccaggc aatgccgtag     120
cttgtgacag cata                                                       134

<210> SEQ ID NO 136
<211> LENGTH: 134
<212> TYPE: DNA
<213> ORGANISM: Artificial Sequence
<220> FEATURE:
<223> OTHER INFORMATION: Synthesized

<400> SEQUENCE: 136
agctatacgg agcatcgtga gattagtcaa ctagcctcgc agatgtataa gcctcgagta      60
ggcatgtagg ctctgatagt accagagctg caacgtctac atgtccaggc aatgccgtag     120
cttgtgacag cata                                                       134

<210> SEQ ID NO 137
<211> LENGTH: 134
<212> TYPE: DNA
<213> ORGANISM: Artificial Sequence
<220> FEATURE:
<223> OTHER INFORMATION: Synthesized

<400> SEQUENCE: 137
agctatacgg agcatcgtga gattagtcaa ctagcctcgc agatgtataa gcctcgagta      60
ggtctgagat gattgatagt accagagcac gcatcactac atgtccaggc aatgccgtag     120
cttgtgacag cata                                                       134

-continued

<210> SEQ ID NO 138
<211> LENGTH: 134
<212> TYPE: DNA
<213> ORGANISM: Artificial Sequence
<220> FEATURE:
<223> OTHER INFORMATION: Synthesized

<400> SEQUENCE: 138
agctatacgg agcatcgtga gattagtcaa ctagcctcgc agatgtataa gcctcgagta        60
gacatgactg cgttgatagt accagagcgt gatgctctac atgtccaggc aatgccgtag       120
cttgtgacag cata                                                          134

<210> SEQ ID NO 139
<211> LENGTH: 134
<212> TYPE: DNA
<213> ORGANISM: Artificial Sequence
<220> FEATURE:
<223> OTHER INFORMATION: Synthesized

<400> SEQUENCE: 139
agctatacgg agcatcgtga gattagtcaa ctagcctcgc agatgtataa gcctcgagta        60
gatcacatga ctctgatagt accagagctg acctagctac atgtccaggc aatgccgtag       120
cttgtgacag cata                                                          134

<210> SEQ ID NO 140
<211> LENGTH: 134
<212> TYPE: DNA
<213> ORGANISM: Artificial Sequence
<220> FEATURE:
<223> OTHER INFORMATION: Synthesized

<400> SEQUENCE: 140
agctatacgg agcatcgtga gattagtcaa ctagcctcgc agatgtataa gcctcgagta        60
ggtcaacgct cattgatagt accagagctg tcacacctac atgtccaggc aatgccgtag       120
cttgtgacag cata                                                          134

<210> SEQ ID NO 141
<211> LENGTH: 134
<212> TYPE: DNA
<213> ORGANISM: Artificial Sequence
<220> FEATURE:
<223> OTHER INFORMATION: Synthesized

<400> SEQUENCE: 141
agctatacgg agcatcgtga gattagtcaa ctagcctcgt catcgtataa gcctcgagta        60
ggcgtagctg tactgatagt accagagcca gaacgactac atgtccaggc aatgccgtag       120
cttgtgacag cata                                                          134

<210> SEQ ID NO 142
<211> LENGTH: 134
<212> TYPE: DNA
<213> ORGANISM: Artificial Sequence
<220> FEATURE:
<223> OTHER INFORMATION: Synthesized

<400> SEQUENCE: 142
agctatacgg agcatcgtga gattagtcaa ctagcctcgt catcgtataa gcctcgagta        60
ggcaggacac tgttgatagt accagagcag catcgactac atgtccaggc aatgccgtag       120
cttgtgacag cata                                                          134

```
<210> SEQ ID NO 143
<211> LENGTH: 134
<212> TYPE: DNA
<213> ORGANISM: Artificial Sequence
<220> FEATURE:
<223> OTHER INFORMATION: Synthesized

<400> SEQUENCE: 143
agctatacgg agcatcgtga gattagtcaa ctagcctcgt catcgtataa gcctcgagta        60
ggacggtcaa gtgtgatagt accagagctg atgctgctac atgtccaggc aatgccgtag       120
cttgtgacag cata                                                          134

<210> SEQ ID NO 144
<211> LENGTH: 134
<212> TYPE: DNA
<213> ORGANISM: Artificial Sequence
<220> FEATURE:
<223> OTHER INFORMATION: Synthesized

<400> SEQUENCE: 144
agctatacgg agcatcgtga gattagtcaa ctagcctcgt catcgtataa gcctcgagta        60
gtgcgcatga cagtgatagt accagagcga tcctgactac atgtccaggc aatgccgtag       120
cttgtgacag cata                                                          134

<210> SEQ ID NO 145
<211> LENGTH: 134
<212> TYPE: DNA
<213> ORGANISM: Artificial Sequence
<220> FEATURE:
<223> OTHER INFORMATION: Synthesized

<400> SEQUENCE: 145
agctatacgg agcatcgtga gattagtcaa ctagcctcgt catcgtataa gcctcgagta        60
gactaatacg tcgtgatagt accagagcac atcgctctac atgtccaggc aatgccgtag       120
cttgtgacag cata                                                          134

<210> SEQ ID NO 146
<211> LENGTH: 134
<212> TYPE: DNA
<213> ORGANISM: Artificial Sequence
<220> FEATURE:
<223> OTHER INFORMATION: Synthesized

<400> SEQUENCE: 146
agctatacgg agcatcgtga gattagtcaa ctagcctcgt catcgtataa gcctcgagta        60
gctaccgact ctgtgatagt accagagcga tgagtgctac atgtccaggc aatgccgtag       120
cttgtgacag cata                                                          134

<210> SEQ ID NO 147
<211> LENGTH: 134
<212> TYPE: DNA
<213> ORGANISM: Artificial Sequence
<220> FEATURE:
<223> OTHER INFORMATION: Synthesized

<400> SEQUENCE: 147
agctatacgg agcatcgtga gattagtcaa ctagcctcgt catcgtataa gcctcgagta        60
gtctcacagt agctgatagt accagagcag cttcagctac atgtccaggc aatgccgtag       120
```

-continued

```
cttgtgacag cata                                                       134

<210> SEQ ID NO 148
<211> LENGTH: 134
<212> TYPE: DNA
<213> ORGANISM: Artificial Sequence
<220> FEATURE:
<223> OTHER INFORMATION: Synthesized

<400> SEQUENCE: 148
agctatacgg agcatcgtga gattagtcaa ctagcctcgt catcgtataa gcctcgagta      60
gcacggtctc gattgatagt accagagcct agctcactac atgtccaggc aatgccgtag     120
cttgtgacag cata                                                       134

<210> SEQ ID NO 149
<211> LENGTH: 134
<212> TYPE: DNA
<213> ORGANISM: Artificial Sequence
<220> FEATURE:
<223> OTHER INFORMATION: Synthesized

<400> SEQUENCE: 149
agctatacgg agcatcgtga gattagtcaa ctagcctcgt catcgtataa gcctcgagta      60
gtcaccactt ctatgatagt accagagcct acacagctac atgtccaggc aatgccgtag     120
cttgtgacag cata                                                       134

<210> SEQ ID NO 150
<211> LENGTH: 134
<212> TYPE: DNA
<213> ORGANISM: Artificial Sequence
<220> FEATURE:
<223> OTHER INFORMATION: Synthesized

<400> SEQUENCE: 150
agctatacgg agcatcgtga gattagtcaa ctagcctcgt catcgtataa gcctcgagta      60
gagctcacag cgttgatagt accagagcta gccactctac atgtccaggc aatgccgtag     120
cttgtgacag cata                                                       134

<210> SEQ ID NO 151
<211> LENGTH: 134
<212> TYPE: DNA
<213> ORGANISM: Artificial Sequence
<220> FEATURE:
<223> OTHER INFORMATION: Synthesized

<400> SEQUENCE: 151
agctatacgg agcatcgtga gattagtcaa ctagcctcgt catcgtataa gcctcgagta      60
gcgaggatca cactgatagt accagagcag tgatgcctac atgtccaggc aatgccgtag     120
cttgtgacag cata                                                       134

<210> SEQ ID NO 152
<211> LENGTH: 134
<212> TYPE: DNA
<213> ORGANISM: Artificial Sequence
<220> FEATURE:
<223> OTHER INFORMATION: Synthesized

<400> SEQUENCE: 152
agctatacgg agcatcgtga gattagtcaa ctagcctcgt catcgtataa gcctcgagta      60
gagcttgacg tattgatagt accagagcca tcatgcctac atgtccaggc aatgccgtag     120
```

-continued

```
cttgtgacag cata                                              134

<210> SEQ ID NO 153
<211> LENGTH: 134
<212> TYPE: DNA
<213> ORGANISM: Artificial Sequence
<220> FEATURE:
<223> OTHER INFORMATION: Synthesized

<400> SEQUENCE: 153
agctatacgg agcatcgtga gattagtcaa ctagcctcgt catcgtataa gcctcgagta      60
gtgagtcaga cattgatagt accagagctg caacgtctac atgtccaggc aatgccgtag     120
cttgtgacag cata                                                      134

<210> SEQ ID NO 154
<211> LENGTH: 134
<212> TYPE: DNA
<213> ORGANISM: Artificial Sequence
<220> FEATURE:
<223> OTHER INFORMATION: Synthesized

<400> SEQUENCE: 154
agctatacgg agcatcgtga gattagtcaa ctagcctcgt catcgtataa gcctcgagta      60
gtagtactgt cgctgatagt accagagcac gcatcactac atgtccaggc aatgccgtag     120
cttgtgacag cata                                                      134

<210> SEQ ID NO 155
<211> LENGTH: 134
<212> TYPE: DNA
<213> ORGANISM: Artificial Sequence
<220> FEATURE:
<223> OTHER INFORMATION: Synthesized

<400> SEQUENCE: 155
agctatacgg agcatcgtga gattagtcaa ctagcctcgt catcgtataa gcctcgagta      60
gtgtgctatc acttgatagt accagagcgt gatgctctac atgtccaggc aatgccgtag     120
cttgtgacag cata                                                      134

<210> SEQ ID NO 156
<211> LENGTH: 134
<212> TYPE: DNA
<213> ORGANISM: Artificial Sequence
<220> FEATURE:
<223> OTHER INFORMATION: Synthesized

<400> SEQUENCE: 156
agctatacgg agcatcgtga gattagtcaa ctagcctcgt catcgtataa gcctcgagta      60
gcacacatct agttgatagt accagagctg acctagctac atgtccaggc aatgccgtag     120
cttgtgacag cata                                                      134
```